(12) United States Patent
O'Connell et al.

(10) Patent No.: US 6,270,768 B1
(45) Date of Patent: Aug. 7, 2001

(54) AZALIDES AND METHODS OF MAKING SAME

(75) Inventors: Thomas N. O'Connell, Mystic; Brook K. Morse, Colchester; Hamish Alastair Irvine McArthur; John Philip Dirlam, both of Gales Ferry, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/491,254

(22) Filed: Jan. 26, 2000

Related U.S. Application Data

(60) Provisional application No. 60/117,631, filed on Jan. 28, 1999.

(51) Int. Cl.$^7$ .......................... A61K 39/395; A61K 39/40; A61K 39/42; C07D 313/00; C07D 407/00
(52) U.S. Cl. .......................... 424/181.1; 549/271; 549/263
(58) Field of Search ..................................... 549/271, 263; 424/181.1

(56) References Cited

U.S. PATENT DOCUMENTS

| | | | |
|---|---|---|---|
| 4,439,426 | 3/1984 | Toscano et al. | 424/181 |

FOREIGN PATENT DOCUMENTS

| | | | |
|---|---|---|---|
| 891733 | * | 12/1998 | (BE) . |
| 56290 | * | 2/1986 | (EP) . |
| 0195960 | | 12/1988 | (EP) . |
| 0180415 | | 1/1990 | (EP) . |
| 0422843 | | 2/1995 | (EP) . |
| 9856801 | * | 12/1998 | (WO) . |

OTHER PUBLICATIONS

Tatsuta et al., J.Antibiot.,40/6, 9103, "Synth.of biosyn-.presursor of oleandomycin . . . ", Jun. 1987.*

Ono, Hideo et al.,JPN. J. Microb. 19/5,343–7,"Drug Resis.in *Staphylococcus aureus*. . . ", Jun. 1987.*

S. Gaisser, et al.; Mol Gen Genet; Analysis of eryBI, eryBVII and eryBVII from the erythromycin biosynthetic gene cluster in *Saccharopolyspora erythraea*; (1998); 258: 78–88.

K. Salah–Bey, et al.; Mol Gen Genet; Targeted Gene Inactivation for the Elucidation of Deoxysugar Biosynthesis in the Erythromycin Producer *Saccharopolyspora erythraea*; (1998); 257: 542–553.

\* cited by examiner

*Primary Examiner*—Richard L. Raymond
*Assistant Examiner*—Sudhaker B. Patel
(74) *Attorney, Agent, or Firm*—Peter C. Richardson; Paul H. Ginsburg; Jeffrey N. Myers

(57) ABSTRACT

This invention relates to methods of preparing compounds of Formula 1:

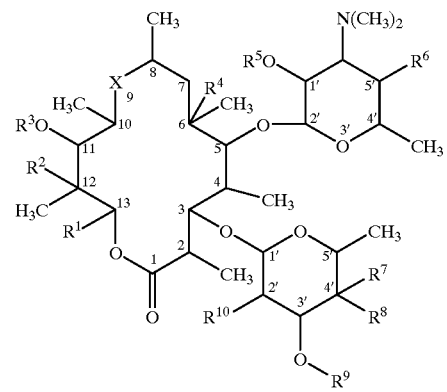

and to pharmaceutically acceptable salts and solvates thereof, and to methods for preparing same. The compounds of Formula 1 are antibacterial agents that may be used to treat various bacterial and protozoal infections, and may also be used to treat cancer. The invention also relates to pharmaceutical compositions comprising the compounds of Formula 1, and to methods of treating sbacterial and protozoal infections by administering compounds of Formula 1.s

33 Claims, No Drawings

AZALIDES AND METHODS OF MAKING SAME

CROSS-REFERENCE TO RELATED APPLICATIONS

This application claims the benefit of U.S. Provisional Application Ser. No. 60/117,631, filed Jan. 28, 1999.

FIELD OF INVENTION

This invention relates to novel azalides that are useful as anticancer agents, antibacterial agents, and antiprotozoa agents, and to methods of making same.

BACKGROUND OF THE INVENTION

Macrolide antibiotics are useful in the treatment of a broad spectrum of bacterial infections and protozoa infections in mammals, fish and birds. These antibiotics include derivatives of erythromycin A, some of which have been formed by the addition of naturally occurring intermediates of erythromycin biogenesis to the fermentation media of *Streptomyces antibioticus* ATCC 31771. Spagnoli, R., et al., *J. Antibiotics,* 34(4):365–375 (1983); U.S. Pat. No. 4,439,426. The resulting oleandrose derivatives are more stable than erythromycin A under acidic conditions.

Other derivatives of erythromycin A include azalides such as azithromycin, the synthesis of which is described by U.S. Pat. Nos. 4,474,768 and 4,517,359. The azalide aglycone contains a nitrogen atom and is structurally, conformationally and electronically distinct from naturally occurring macrolide aglycones. Prior to the invention, it was believed that biological cultures would not glycosilate this unnatural macrolide aglycone.

SUMMARY OF THE INVENTION

The invention is directed to compounds of Formula 1:

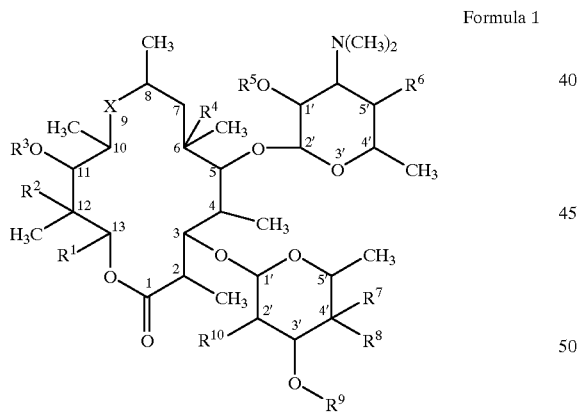

Formula 1 and to pharmaceutically acceptable salts and solvates thereof, wherein:

X is —$CH_2N(R_1)$—, —$N(R^a)CH_2$—, or —C(O)— wherein the first dash of each of the foregoing X groups is attached to the C-10 carbon of the compound of Formula 1 and the last dash of each group is attached to the C-8 carbon of the compound of Formula 1, and $R^a$ is H, $C_1$–$C_{10}$ alkyl, $C_2$–$C_{10}$ alkenyl, $C_2$–$C_{10}$ alkynyl, —$(CH_2)_m(C_6$–$C_{10}$ aryl), and —$(CH_2)_m$(5–10 membered heteroaryl), wherein m is an integer ranging from 0 to 4;

$R^1$ is straight-chain or alpha-branched $C_1$–$C_8$ alkyl, alkenyl, alkynyl, alkoxyalkyl or alkylthioalkyl group any of which may be substituted by one or more hydroxyl groups; a $C_3$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms; or a 3 to 6 membered oxygen or sulphur containing heterocyclic ring which may be saturated, or fully or partially unsaturated, and which may be substituted by one or more $C_1$–$C_4$ alkyl groups or halo atoms or a group of the formula $SR^b$, wherein $R^b$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo or a 3 to 6 membered oxygen or sulfur containing heterocyclic ring which may be saturated, or fully or partially unsaturated and which may be substituted by one or more $C_1$–$C_4$ alkyl groups or halo atoms;

or $R^1$ is phenyl which may be substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano;

or $R^1$ is of the formula

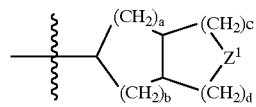

wherein $Z^1$ is O, S or —$CH_2$—, and a, b, c, and d is each independently an integer ranging from 0 to 2 and a+b+c+d#5;

$R^2$ is H or OH;

$R^3$ is —$C(O)NR^cR^d$, wherein each of $R^c$ and $R^d$ is independently H, $C_1$–$C_{10}$ alkyl, $C_2$–$C_{20}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein each of the foregoing $R^c$ and $R^d$ groups, except H, may be substituted by 1 to 3 Q groups; or wherein $R^c$ and $R^d$ may be taken together to form a 4–7 membered saturated ring or a 5–10 membered heteroaryl ring, wherein said saturated and heteroaryl rings may include 1 or 2 heteroatoms selected from O, S and N, in addition to the nitrogen to which $R^c$ and $R^d$ are attached, and said saturated ring may include 1 or 2 carbon-carbon double or triple bonds, and said saturated and heteroaryl rings may be substituted by 1 to 3 Q groups;

or $R^2$ and $R^3$ taken together form a carbonate ring;

$R^4$ is H, OH, O($C_1$–$C_{10}$ alkyl);

$R^5$ is H, —$C(O)R^e$, —C(O)$OR^e$, —$C(O)NR^eR^f$, or a hydroxy protecting group, and $R^e$ and $R^f$ is each independently H or $C_1$–$C_6$ alkyl;

$R^6$ is H or OH;

$R^7$ is H or OH;

$R^8$ is $C_1$–$C_{10}$ alkyl, $C_2$–$C_{20}$ alkenyl, $C_2$–$C_{10}$ alkynyl, cyano, —$CH_2S(O)_nR^g$ wherein n is an integer ranging from 0 to 2, —$CH_2OR^g$, —$CH_2N(OR^h)R^g$, —$CH_2NR^gR^i$, —$(CH_2)_m(C_6$–$C_{12}$ aryl), or —$(CH_2)_m$(5–10 membered heteroalkyl), wherein m is an integer ranging from 0 to 4, and wherein the foregoing $R^8$ groups may be substituted by 1 to 3 Q groups;

each $R^g$ is independently H, $C_1$–$C_{10}$ alkyl, $C_2$–$C_{10}$ alkenyl, $C_2$–$C_{10}$ alkynyl, —$(CH_2)_qCR^{g(1)}R^{g(2)}$ $(CH_2)_rNR^{g(3)}R^{g(4)}$ wherein q and r is each independently an integer ranging from 0 to 3 except q and r are not both 0, —(CH$_2$)$_m$(C$_6$–C$_{10}$ aryl), or —(CH$_2$)$_m$(5–10 membered heteroaryl), wherein m is an integer ranging from 0 to 4, and wherein the foregoing R$^g$ groups, except H, may be substituted by 1 to 3 Q groups;

each of R$^{g(1)}$, R$^{g(2)}$, R$^{g(3)}$ and R$^{g(4)}$ is independently selected from H, C$_1$–C$_{10}$ alkyl, —(CH$_2$)$_m$(C$_6$–C$_{10}$ aryl), or —(CH$_2$)$_m$(5–10 membered heteroaryl), wherein m is an integer ranging from 0 to 4, and wherein the foregoing R$^{g(1)}$, R$^{g(2)}$, R$^{g(3)}$ and R$^{g(4)}$ groups, except H, may be substituted by 1 to 3 Q groups;

or R$^{g(1)}$ and R$^{g(3)}$ are taken together to form —(CH$_2$)$_p$— wherein p is an integer ranging from 0 to 3 such that a 4–7 membered saturated ring is formed that may include 1 or 2 carbon-carbon double or triple bonds;

or R$^{g(3)}$ and R$^{g(4)}$ are taken together to form a 4–10 membered monocyclic or polycyclic saturated ring or a 5–10 membered heteroaryl ring, wherein said saturated and heteroaryl rings may include 1 or 2 heteroatoms selected from O, S and N, in addition to the nitrogen to which R$^{g(3)}$ and R$^{g(4)}$ are attached, said saturated ring may include 1 or 2 carbon-carbon double or triple bonds, and said saturated and heteroaryl rings may be substituted by 1 to 3 Q groups;

R$^h$ is H or C$_1$–C$_6$ alkyl;

R$^i$ is H, C$_1$–C$_{10}$ alkyl, C$_2$–C$_{10}$ alkenyl, or C$_2$–C$_{10}$ alkynyl, wherein the foregoing R$^i$ group may be substituted by 1 to 3 substituents independently selected from halo, OH, and O(C$_1$–C$_6$ alkyl);

and if R$^8$ is —CH$_2$NR$^g$R$^i$, then R$^g$ and R$^i$ may be taken together to form a 4–10 membered saturated monocyclic or polycycic saturated ring or a 5–10 membered heteroaryl ring, wherein said saturated and heteroaryl rings optionally include 1 or 2 heteroatoms selected from O, S and N, in addition to the nitrogen to which R$^g$ and R$^i$ are attached, said saturated ring may include 1 or 2 carbon-carbon double or triple bonds, and said saturated and heteroaryl rings may be substituted by 1 to 3 Q groups;

or R$^7$ and R$^8$ are taken together to form an oxazolyl ring as shown below

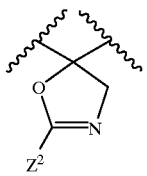

wherein Z$^2$ is —SR$^g$, —(CH$_2$)$_n$C(O)R$^g$ wherein n is 0 or 1, C$_1$–C$_{10}$ alkyl, C$_2$–C$_{10}$ alkenyl, C$_2$–C$_{10}$ alkynyl, —(CH$_2$)$_m$(C$_6$–C$_{10}$ aryl), or —(CH$_2$)$_m$(5–10 membered heteroaryl), wherein m is an integer ranging from 0 to 4, and wherein the foregoing Z$^2$ groups may be substituted by 1 to 3 Q groups;

each Q is independently selected from halo, cyano, nitro, trifluoromethyl, azido, —C(O)Q$^1$, —OC(O)Q$^1$, —C(O)OQ$^1$, —OC(O)OQ$^1$, —NQ$^2$C(O)Q$^3$, —C(O)NQ$^2$Q$^3$, —NQ$^2$Q$^3$, hydoxy, C$_1$–C$_6$ alkyl, C$_1$–C$_6$ alkoxy, —(CH$_2$)$_m$(C$_6$–C$_{10}$ aryl), and —(CH$_2$)$_m$(5–10 membered heteroaryl), wherein m is an integer ranging from 0 to 4, and wherein said aryl and heteroaryl substituents may be substituted by 1 or 2 substituents independently selected from halo, cyano, nitro, trifluoromethyl, azide, —C(O)Q$^1$, —C(O)OQ$^1$, —OC(O)OQ$^1$, —NQ$^2$C(O)Q$^3$, —C(O)NQ$^2$Q$^3$, —NQ$^2$Q$^3$, hydroxy, C$_1$–C$_6$ alkyl, and C$_1$–C$_6$ alkoxy;

each Q$^1$, Q$^2$ and Q$^3$ is independently selected from H, OH, C$_1$–C$_{10}$ alkyl, C$_1$–C$_6$ alkoxy, C$_2$–C$_{10}$ alkenyl, C$_2$–C$_{10}$ alkynyl, —(CH$_2$)$_m$(C$_6$–C$_{10}$ aryl), and —(CH$_2$)$_m$(5–10 membered heteroaryl), wherein m is an integer ranging from 0 to 4;

R$^9$ and is H or CH$_3$; and

R$^{10}$ is H or CH$_3$.

In a preferred compound of Formula 1, R$^9$ is not CH$_3$ if X is —CH$_2$N(R$^a$)— or —N(R$^a$)CH$_2$—, R$^6$ is H, and R$^{10}$ is CH$_3$.

In another preferred compound of Formula 1, R$^9$ is not CH$_3$ if X is —C(O)—, R$^4$ is OH or CH$_3$, R$^6$ is H, and R$^{10}$ is CH$_3$.

Preferred compounds of Formula 1 include those wherein X is —CH$_2$N(R$^a$)— or —N(R$^a$)CH$_2$—.

Preferred compounds of Formula 1 include those wherein R$^a$ is H or CH$_3$.

Preferred compounds of Formula 1 include those wherein R$^1$ is ethyl, isopropyl, sec-butyl, cyclopropyl, cyclobutyl, cyclopentyl, methylthioethyl and 3-furyl.

Preferred compounds of Formula 1 also include those wherein R$^2$ is OH.

Preferred compounds of Formula 1 also include those wherein is H.

Preferred compounds of Formula 1 also include those wherein R$^4$ is H, OH, or OCH$_3$.

Preferred compounds of Formula 1 also include those wherein R$^5$ is H, OH or OCH$_3$.

Preferred compounds of Formula 1 also include those wherein R$^6$ is H.

Preferred compounds of Formula 1 also include those wherein R$^7$ is H.

Preferred compounds of Formula 1 also include those wherein R$^8$ is H or OH.

Preferred compounds of Formula 1 also include those wherein R$^9$ is H or CH$_3$.

Preferred compounds of Formula 1 also include those wherein R$^{10}$ is H.

More preferred compounds of Formula 1 include those wherein:

R$^2$ is H, R$^7$ is H, R$^8$ is OH, and R$^1$ is methyl, ethyl, isopropyl, cyclopropyl, sec-butyl, methylthioethyl, or 3-furyl.

More preferred compounds of Formula 1 further include those wherein R$^4$ is hydroxy, R$^5$ is H, R$^7$ is hydroxy, and R$^8$ is —CH$_2$NR$^9$R$^i$ or —CH$_2$SR$^g$.

More preferred compounds of Formula 1 also include those wherein R$^4$ is hydroxy, R$^5$ is H, R$^7$ is hydroxy, R$^8$ is —CH$_2$NR$^g$R$^i$ or —CH$_2$SR$^g$, and R$^i$ and R$^g$ are each selected from H, C$_1$–C$_{10}$ alkyl, C$_2$–C$_{10}$ alkenyl, and C$_2$–C$_{10}$ alkynyl, wherein the R$^i$ and R$^g$ groups, except H, may be substituted by 1 or 2 substituents independently selected from hydroxy, halo and C$_1$–C$_6$ alkoxy. Specific preferred compounds having the foregoing general structure include those wherein R$^i$ is either H or is selected from the following groups from which R$^g$ is also independently selected: methyl, ethyl, allyl, n-butyl, isobutyl, 2-methoxyethyl, cyclopentyl, cyclobutyl, 3-methoxypropyl, 3-ethoxypropyl, n-propyl, isopropyl, 2-hydroxyethyl, cyclopropyl, 2,2,2-trifluoroethyl, 2-propynyl, sec-butyl, tert-butyl, and n-hexyl.

More preferred compounds of Formula 1 further include those wherein R$^4$ is hydroxy, R$^5$ is H, R$^7$ is hydroxy, R$^8$ is —CH$_2$NHR$^g$, and R$^g$ is —(CH$_2$)$_m$(C$_6$–C$_{10}$ aryl) wherein m is an integer ranging from 0 to 4. Specific preferred compounds having the foregoing general structure include those wherein $R^g$ is phenyl or benzyl.

More preferred compounds of Formula 1 further include those wherein $R^4$ is hydroxy, $R^5$ is H, $R^7$ is hydroxy, $R^8$ is —$CH_2NHR^g$, and $R^i$ and $R^g$ are taken together to form a saturated ring. Specific preferred compounds having the foregoing general structure include those wherein $R^i$ and $R^g$ are taken together to form a piperidino, trimethyleneimino, or morpholino ring.

More preferred compounds of Formula 1 also include those wherein $R^4$ is hydroxy, $R^5$ is H, $R^7$ is hydroxy, $R^8$ is —$CH_2NHR^g$, and $R^i$ and $R^g$ are taken together to form a heteroaryl ring that may be substituted by 1 or 2 $C_1$–$C_6$ alkyl groups. Specific preferred compounds having the foregoing general structure include those wherein $R^i$ and $R^g$ are taken together to form a pyrrolidino, triazolyl, or imidazolyl ring wherein said heteroaryl groups may be substituted by 1 or 2 methyl groups.

More preferred compounds of Formula 1 also include those wherein $R^4$ is hydroxy, $R^5$ is H, $R^7$ is hydroxy, $R^8$ is —$CH_2SR^g$, and $R^g$ is selected from $C_1$–$C_{10}$ alkyl, $C_2$–$C_{10}$ alkenyl, and $C_2$–$C_{10}$ alkynyl, wherein said $R^g$ groups may be substituted by 1 or 2 substituents independently selected from hydroxy, halo and $C_1$–$C_6$ alkoxy. Specific preferred compounds having the foregoing general structure include those wherein $R^g$ is methyl, ethyl or 2-hydroxyethyl.

More preferred compounds of Formula 1 further include those wherein $R^4$ is hydroxy, $R^5$ is H, $R^7$ is hydroxy, and $R^8$ is selected from $C_1$–$C_{10}$ alkyl, $C_2$–$C_{10}$ alkenyl, and $C_2$–$C_{10}$ alkynyl, wherein said $R^8$ groups may be substituted with 1 or 2 substituents independently selected from hydroxy, —$C(O)Q^1$, —$NQ^2Q^3$, halo, cyano, azido, 5–10 membered heteroaryl, and $C_1$–$C_6$ alkoxy. Specific preferred compounds having the foregoing general structure include those wherein $R^8$ is methyl, allyl, vinyl, ethynyl, 1-methyl-2-propenyl, 3-methoxy-1-propynyl, 3-dimethylamino-1-propynyl, 2-pyridylethynyl, 1-propynyl, 3-hydroxy-1-propynyl, 3-hydroxy-1-propenyl, 3-hydroxypropyl, 3-methoxy-1-propenyl, 3-methoxypropyl, 1-propynyl, n-butyl, ethyl, propyl, 2-hydroxyethyl, formylmethyl, 6cyano-1-pentynyl, 3-dimehtylamino-1-propenyl, or 3-dimethylaminopropyl.

More preferred compounds of Formula 1 further include those wherein $R^4$ is hydroxy, $R^5$ is H, $R^7$ is hydroxy, and $R^8$ is —$(CH_2)_m$(5–10 membered heteroaryl) wherein m is an integer ranging from 0 to 4. Specific preferred compounds having the foregoing general structure include those wherein $R^8$ is 2-thienyl, 2-pyridyl, 1-methyl-2-imidazolyl, 2-furyl, or 1-methyl-2-pyrrolyl.

More preferred compounds of Formula 1 also include those wherein $R^4$ is hydroxy, $R^5$ is H, $R^7$ is hydroxy, and $R^8$ is —$(CH_2)_m$(5–10 membered aryl) wherein m is an integer ranging from 0 to 4. Specific preferred compounds having the foregoing general structure include those wherein $R^8$ is phenyl.

More preferred compounds of Formula 1 also include those wherein $R^7$ and $R^8$ are itaken together to form an oxazolyl ring as shown below

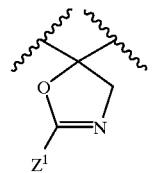

and wherein $Z^1$ is as defined above.

More preferred compounds of Formula 1 also include those wherein $R^8$ is of the formula:

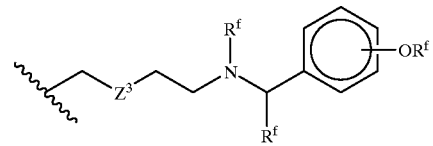

wherein $Z^3$ is O, S, or —$N(R^i)$—, and wherein the —$OR^h$ group may be attached at any available carbon on the phenyl group.

Most preferred compounds of Formula 1 include those wherein:

X=—$N(H)CH_2$—, $R^1$ is —$CH_2CH_3$, $R^2$ is OH, $R^3$ is H, $R^4$ is OH, $R^5$ is H, $R^6$ is H, $R^7$ is OH, $R^9$ is H, $R^{10}$ is H, and $R^8$ is H, —$CH_2$(n-butylamino), —$CH_2$(propylamino), —$CH_2$(methoxyethylamino), —$CH_2$(dimethylamino), —$CH_2$(cyclopropylamino), —$CH_2$(allylamino), —$CH_2$(imidazol-1 -yl), —$CH_2$(2,2,2-trifluoroethylamino), —$CH_2$(bis(2-hydroxyethyl)amino), —$CH_2$(bis(2-methoxyethyl)amino), —$CH_2$(mercapto), —$CH_2$(4-methylimidazol-1-yl), —$CH_2$(2-propynylamino), —$CH_2$(diallylamino), —$CH_2$(1,2,3-triazol-1-yl), —$CH_2$(2-methylimidazol-1-yl), or —$CH_2$(1,2,4-triazol-1-yl);

X=—$N(CH_3)CH_2$—, $R^1$ is —$CH_2CH_3$, $R^2$ is OH, $R^3$ is H, $R^4$ is OH, $R^5$ is H, $R^6$ is H, $R^7$ is OH, $R^9$ is H, $R^{10}$ is H, and $R^8$ is H, —$CH_2$(n-butylamino), —$CH_2$(propylamino), —$CH_2$(methoxyethylamino), —$CH_2$(dimethylamino), —$CH_2$(cyclopropylamino), —$CH_2$(allylamino), —$CH_2$(imidazol-1-yl), —$CH_2$(2,2,2-trifluoroethylamino), —$CH_2$(bis(2-hydroxyethyl)amino), —$CH_2$(bis(2-methoxyethyl)amino), —$CH_2$(mercapto), —$CH_2$(4-methylimidazol-1-yl), —$CH_2$(2-propynylamino), —$CH_2$(diallylamino), —$CH_2$(1,2,3-triazol-1-yl), —$CH_2$(2-methylimidazol-1-yl), or —$CH_2$(1,2,4-triazol-1-yl);

X=—$N(CH_2CH_3)CH_2$—, $R^1$ is —$CH_2CH_3$, $R^2$ is OH, $R^3$ is H, $R^4$ is OH, $R^5$ is H, $R^6$ is H, $R^7$ is OH, $R^9$ is H, $R^{10}$ is H, and $R^8$ is H, —$CH_2$(n-butylamino), —$CH_2$(propylamino), —$CH_2$(methoxyethylamino), —$CH_2$(dimethylamino), —$CH_2$(cyclopropylamino), —$CH_2$(allylamino), —$CH_2$(imidazol-1-yl), —$CH_2$(2,2,2-trifluoroethylamino), —$CH_2$(bis(2-hydroxyethyl)amino), —$CH_2$(bis(2-methoxyethyl)amino), —$CH_2$(mercapto), —$CH_2$(4-methylimidazol-1-yl), —$CH_2$(2-propynylamino), —$CH_2$(diallylamino), —$CH_2$(1,2,3-triazol-1-yl), —$CH_2$(2-methylimidazol-1-yl), or —$CH_2$(1,2,4-triazol-1-yl);

X=—$N(CH_2CH_2CH_3)CH_2$—, $R^1$ is —$CH_2CH_3$, $R^2$ is OH, $R^3$ is H, $R^4$ is OH, $R^5$ is H, $R^6$ is H, $R^7$ is OH, $R^9$ is H, $R^{10}$ is H, and $R^8$ is H, —$CH_2$(n-butylamino), —$CH_2$(propylamino), —$CH_2$(methoxyethylamino), —$CH_2$(dimethylamino), —$CH_2$(cyclopropylamino), —$CH_2$(allylamino), —$CH_2$(imidazol-1-yl), —$CH_2$(2,2,2-trifluoroethylamino), —$CH_2$(bis(2-hydroxyethyl)amino), —$CH_2$(bis(2-methoxyethyl)amino), —$CH_2$(mercapto), —$CH_2$(4-methylimidazol-1-yl), —$CH_2$(2-propynylamino), —$CH_2$(diallylamino), —$CH_2$(1,2,3-triazol-1-yl), —$CH_2$(2-methylimidazol-1-yl), or —$CH_2$(1,2,4-triazol-1-yl); and X=—N(CH$_2$CH$_2$CH$_2$CH$_3$)CH$_2$—, R$^1$ is —CH$_2$CH$_3$, R$^2$ is OH, R$^3$ is H, R$^4$ is OH, R$^5$ is H, R$^6$ is H, R$^7$ is OH, R$^9$ is H, R$^{10}$ is H, and R$^8$ is H, —CH$_2$(n-butylamino), —CH$_2$(propylamino), —CH$_2$(methoxyethylamino), —CH$_2$(dimethylamino), —CH$_2$(cyclopropylamino), —CH$_2$(allylamino), —CH$_2$(imidazol-1-yl), —CH$_2$(2,2,2-trifluoroethylamino), —CH$_2$(bis(2-hydroxyethyl)amino), —CH$_2$(bis(2-methoxyethyl)amino), —CH$_2$(mercapto), —CH$_2$(4-methylimidazol-1-yl), —CH$_2$(2-propynylamino), —CH$_2$(diallylamino), —CH$_2$(1,2,3-triazol-1-yl), —CH$_2$(2-methylimidazol-1-yl), or —CH$_2$(1,2,4-triazol-1-yl);

The invention also relates to pharmaceutical compositions comprising a therapeutically effective amount of a compound of Formula 1, or a pharmaceutically acceptable salt or solvate thereof, and a pharmaceutically acceptable carrier. These pharmaceutical compositions are suitable for the treatment of cancer or bacterial or protozoa infections in mammals, fish or birds.

The invention further relates to methods of treating, mitigating or preventing bacterial or protozoa infections in mammals, fish or birds which comprise the administration of a therapeutically effective amount of a compound of Formula 1, or a pharmaceutically acceptable salt or solvate thereof.

The invention further relates to methods of treating, mitigating or preventing cancer in mammals, fish or birds which comprise the administration of a therapeutically effective amount of a compound of Formula 1, or a pharmaceutically acceptable salt or solvate thereof.

The invention is also directed to methods of preparing an azalide having at least one sugar comprising contacting an azalide aglycone compound with a biological culture under conditions suitable for the formation of an azalide having at least one sugar; and isolating from the biological culture the azalide having at least one sugar.

It is preferred that the at least one sugar be oleandrose or an oleandrose derivative.

It is also preferred that the at least one sugar be cladinose or a cladinose derivative.

It is also preferred that the at least one sugar be mycaminose or a mycaminose derivative.

It is also preferred that the at least one sugar be desosemine or a desosemine deriivative It is also preferred that the biological culture be of *Streptomyces antibioticus* ATCC 202189, *Saccharopolyspora erythraea* ATCC 202199, or a blocked mutant of a *Saccharopolyspora erythraea* strain comprising at least one eryCIV or eryBIII mutation, or a mixture of at least one eryCIV and at least one eryBIII mutation.

One embodiment of this invention is a method of making a compound of Formula 2:

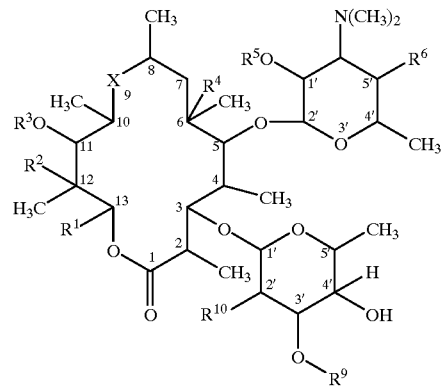

Formula 2 wherein X, R$^1$, R$^2$, R$^3$, R$^4$, R$^5$, R$^6$, R$^9$, and R$^{10}$ are defined above; comprising ntacting a compound of Formula 3:

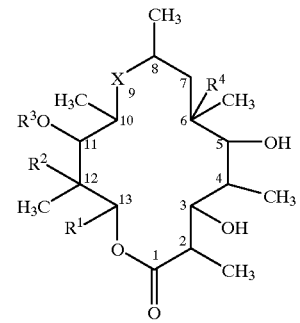

Formula 3 wherein X, R$^1$, R$^2$, R$^3$, and R$^4$ are defined above, with a biological culture under conditions suitable for the formation of the compound of Formula 2.

It is preferred that X be —CH$_2$N(R$^a$)— or —N(R$^a$)CH$_2$—.

It is also preferred that the biological culture be of *Streptomyces antibioticus* ATCC 202189, *Saccharopolyspora erythraea* ATCC 202199, or a blocked mutant of a *Saccharopolyspora erythraea* strain comprising at least one eryCIV or eryBIII mutation, or a mixture of at least one eryCIV and at least one eryBIII mutation.

The compound of Formula 3 may be prepared from a compound of Formula 4:

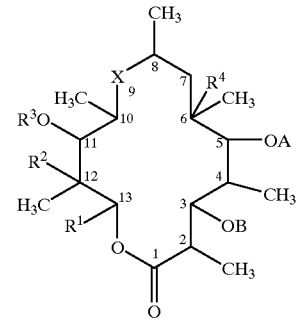

Formula 4 wherein X, $R^1$, $R^2$, $R^3$, and $R^4$ are defined above; A is of the formula:

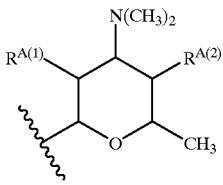

wherein each of $R^{A(1)}$ and $R^{A(1)}$ is independently H, OH, $C_1$–$C_6$ alkyl, aldehyde, ketone, ester, carboxylic acid, carbamate, or derivatives thereof; and B is a sugar. Preferably, B is of the fornula:

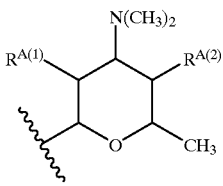

wherein each of $R^{B(1)}$ and $R^{B(2)}$ is independently H, OH, $C_1$–$C_6$ alkyl, aldehyde, ketone, ester, carboxylic acid, amine, or derivatives thereof, and each of $R^{B(3)}$ and $R^{B(4)}$ is independently H or $CH_3$.

DEFINITIONS

The term "treatment," as used herein, unless otherwise indicated, includes the treatment or prevention of cancer or a bacterial infection or protozoal infection as provided in the method of the invention.

As used herein the terms "bacterial infection(s)" and "protozoal infection(s)" include bacterial infections and protozoal infections that occur in mammals, fish and birds as well as disorders related to bacterial infections and protozoal infections that may be treated or prevented by administering antibiotics such as the compounds of the invention. Such bacterial infections and protozoal infections, and disorders related to such infections, include the following: pneumonia, otitis media, sinusitis, bronchitis, tonsillitis and mastoiditis related to infection by *Staphylococcus pneumoniae, Haemophilus influenzae, Moraxella catarrhalis, Staphlococcus aureus*, or *Peptostreptococcus* spp.; pharynigis, rheumatic fever and glomerulonephritis related to infection by *Streptococcus pyogenes*, Groups C and G streptococci, *Clostridium diptheriae*, or *Actinobacillus haemolyticum;* respiratory tract infections related to infection by *Mycoplasma pneumoniae, Legionella pneumophila, Streptococcus pneumoniae, Haemophilus influenzae*, or *Chiamydia pneumoniae;* uncomplicated skin and soft tissue infections, abscesses and osteomyelitis, and puerperal fever related to infection by *Staphlococcus aureus,* coagulase-positive staphlococci (i.e., *S. epidermis., S. hemolyticus,* etc.), *Staphylococcus pyogenes, Streptococcus agalactiae*, Streptococcal groups C–F (minute-colony streptococci), viridans streptococci, *Corynebacterium minutissimum,* Clostridium spp., or *Bartonella henselae;* uncomplicated acute urinary tract infections related to infection by *Staphylococcus saprophyticus* or Enterococcus spp.; urethritis and cervicitis; and sexually transmitted diseases related to infection by *Chiamydia trachomatis, Haemophilus ducreyi, Treponema pallidum, Ureaplasma urealyticum,* or *Neiserria gonorrhea;* toxin diseases related to infection by *S. aureus* (food poisoning and Toxic Shock Syndrome), or Groups A, B and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae*, or Listeria spp.; disseminated *Mycobacterium avium complex* (MAC) disease related to infection by *Mycobacterium avium,* or *Mycobacterium intracellulare;* gastroenteritis related to infection by *Campylobacter jejuni;* intestinal protozoa related to infection by Cryptosporidium spp.; odontogenic infection related to infection by viridans streptococci; persistent cough related to infection by *Bordetella pertussis;* gas gangrene related to infection by *Clostridium perfringens* or Bacteroides spp.; and atherosclerosis related to infection by *Helicobacter pylori* or *Chlamydia pneumoniae.* Bacterial infections and protozoal infections and disorders related to such infections that may be treated or prevented in animals include the following: bovine respiratory disease related to infection by *P. haem., P. multocida, Mycoplasma bovis,* or Bordetella spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae,* Klebsiella spp., Corynebacterium, or Enterococcus spp.; swine respiratory disease related to infection by *A. pleuro., P. multocida* or Mycoplasma spp.; swine enteric disease related to infection by *E. coli, Lawsonia intracellularis,* Salmonella, or *Seipulina hyodyisintedae;* cow footrot related to infection by Fusobacterium spp.; cow metritis related to infection by *E. coli,* cow hairy warts related to infection by *Fusobacterium necrophorum* or *Bacteroides nodosus;* cow pink-eye related to infection by *Moraxella bovis;* cow premature abortion related to infection by protozoa (i.e., neosporium) urinary tract infection in dogs and cats related to infection by *E. coli;* skin and soft tissue infections in dogs and cats related to infection by *Staph. epidermidis, Staph. intermedius, coagulase neg. Staph.* or *P. multocida;* and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections and disorders related to such infections that may be treated or prevented in accord with the methods of the invention are referred to in Sanford, J. P., et al., "The Sanford Guide To Antimicrobial Therapy," $27^{th}$ Edition (Antimicrobial Therapy, Inc., 1996).

The term "halo", as used herein includes fluoro, chloro, bromo or iodo.

The term "alkyl", as used herein includes saturated monovalent hydrocarbon radicals having straight, cyclic or branched moieties, or mixtures thereof. It is to be understood that where cyclic moieties are intended, at least three carbons in said alkyl must be present. Such cyclic moieties include cyclopropyl, cyclobutyl and cyclopentyl.

The term "alkoxy", as used herein includes —O-alkyl groups wherein alkyl is as defined above.

The term "aryl", as used herein includes an organic radical derived from an aromatic hydrocarbon by removal of one hydrogen, such as phenyl or naphthyl.

The term "5–10 membered heteroaryl", as used herein includes aromatic heterocyclic groups containing one or more heteroatoms each selected from O, S and N, wherein each heterocyclic group has from 5 to 10 atoms in its ring system. Examples of suitable 5–10 membered heteroaryl groups include pyridinyl, imidazolyl, pyrimidinyl, pyrazolyl, (1,2,3)- and (1,2,4)-triazolyl, pyrazinyl, tetrazolyl, furyl, thienyl, isoxazolyl, oxazolyl, pyrrolyl and thiazolyl.

The phrase "pharmaceutically acceptable salt(s)", as used herein includes salts of acidic or basic groups which may be present in the compounds of the invention. The compounds of the invention that are basic in nature are capable of forming a wide variety of salts with various inorganic and organic acids. The acids that may be used to prepare pharmaceutically acceptable acid addition salts of such basic compounds of the invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis(2-hydroxy-3-naphthoate)] salts. The compounds of the invention that include an amino moiety may form pharmaceutically acceptable salts with various amino acids, in addition to the acids mentioned above.

Those compounds of the invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the invention.

As used herein, the term "protected form(s)" when used in relation to a particular chemical moiety means a derivative of that moiety that is not reactive under certain conditions. Examples of protecting groups include, but are not limited to, those referred to by Greene, T. W., and Wuts, P. G. M., "Protective Groups In Organic Synthesis," (J. Wiley & Sons, 1991).

The term "hydroxy protecting group," as used herein, includes acetyl, benzyloxycarbonyl, and various hydroxy protecting groups familiar to those skilled in the art including those referred to by Greene, T. W., and Wuts, P. G. M., "Protective Groups In Organic Synthesis," (J. Wiley & Sons, 1991).

As used herein, the term "oleandrose derivative" when used to describe a chemical moiety means a derivative of oleandrose formed by synthetic means known to those skilled in the art and includes, but is not limited to, protected forms of oleandrose.

As used herein, the term "cladinose derivative" when used to describe a chemical moiety means a derivative of cladinose formed by synthetic means known to those skilled in the art and includes, but is not limited to, protected forms of cladinose.

As used herein, the term "desosamine derivative" when used to describe a chemical moiety means a derivative of desosamine formed by synthetic means known to those skilled in the art and includes, but is not limited to, protected forms of desosamine.

As used herein, the term "mycaminose derivative" when used to describe a chemical moiety means a derivative of mycaminose formed by synthetic means known to those skilled in the art and includes, but is not limited to, protected forms of mycaminose.

As used herein, the term "synthetic precursor(s)" when used in relation to a particular chemical moiety refers to a different chemical moiety which may, by synthetic means known to those skilled in the art and with a minimum of experimentation, be converted into the particular chemical moiety. For example, a synthetic precursor of methoxy is hydroxy; a synthetic precursor of hydroxy is methoxy; and a synthetic precursor of a carboxylic acid is an ortho ester. These and other conventional transformations are described, for example, by March, J., "Advanced Organic Chemistry" 3rd ed. (1985).

DETAILED DESCRIPTION OF THE INVENTION

The invention is directed to compounds of Formula 1:

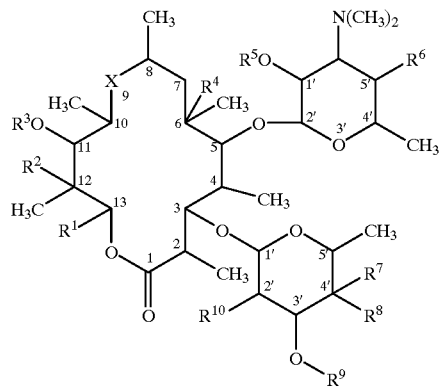

Formula 1 wherein X, $R^1$, $R^2$, $R^3$, $R^4$, $R^5$, $R^6$, $R^7$, $R^8$, $R^9$, and $R^{10}$ are as defined in the Summary of the Invention above, and pharmaceutically acceptable salts and solvates thereof. As these compounds may have asymmetric centers and therefore exist in different enantionmeric and diastereomic forms, all such forms capable of being produced by the methods of this invention are encompassed by this invention.

The compounds of this invention (i.e., compounds of Formula 1 and pharmaceutically acceptable salts and solvates thereof) exhibit antibiotic activity, and may be used as precursors and/or prodrugs of antibiotics. They may also be used as anti-cancer agents. A particular advantage of the compounds of this invention is their increased acid stability as compared to other azalides, particularly those comprising cladinose such as azithromycin. This increased stability increases the shelf-life of the compounds and pharmaceutical compositions comprising them. The increased stability may also increase the pharmokinetic stability of the compounds.

This invention is further directed to pharmaceutical compositions comprising compounds of Formula 1 and pharmaceutically acceptable salts and solvates thereof.

The invention also encompasses methods of preventing, treating and alleviating bacterial infections and protozoal infections in mammals, fish and birds. These methods comprise the administration of a pharmaceutically effective amount of a compound of Formula 1, or a pharmaceutically acceptable salt or solvate thereof, to a mammal, fish or bird in need of such treatment.

The invention also encompasses methods of preventing, treating and alleviating cancer in mammals, fish and birds. These methods comprise the administration of a pharmaceutically effective amount of a compound of Formula 1, or a pharmaceutically acceptable salt or solvate thereof, to a mammal, fish or bird in need of such treatment.

The compounds of this invention may be prepared according to Schemes 1–2 below and the description that follows. Substituents X, $R^1$, $R^2$, $R^3$ $R^4$, $R^5$, $R^6$, $R^7$, $R^8$, $R^9$, and $R^{10}$ are as defined in the Summary of the Invention unless otherwise indicated.

Scheme I

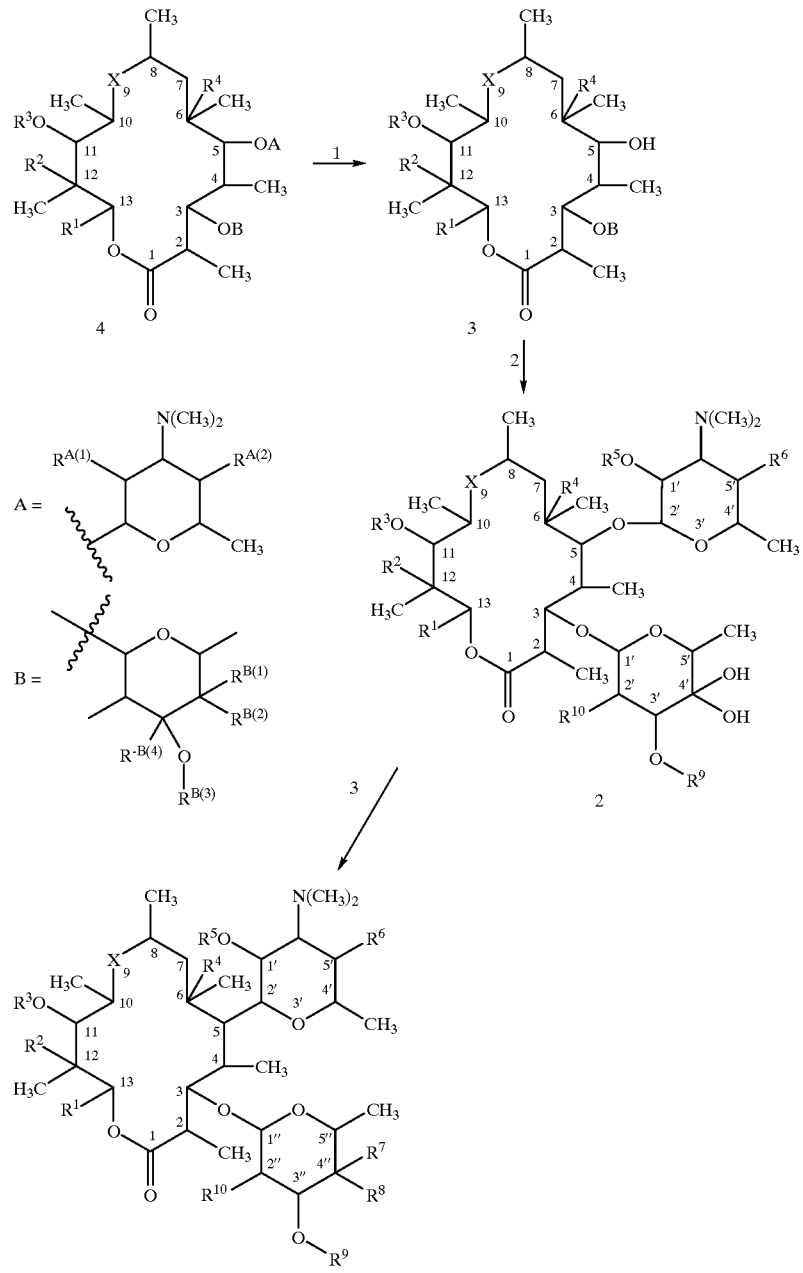

Scheme II

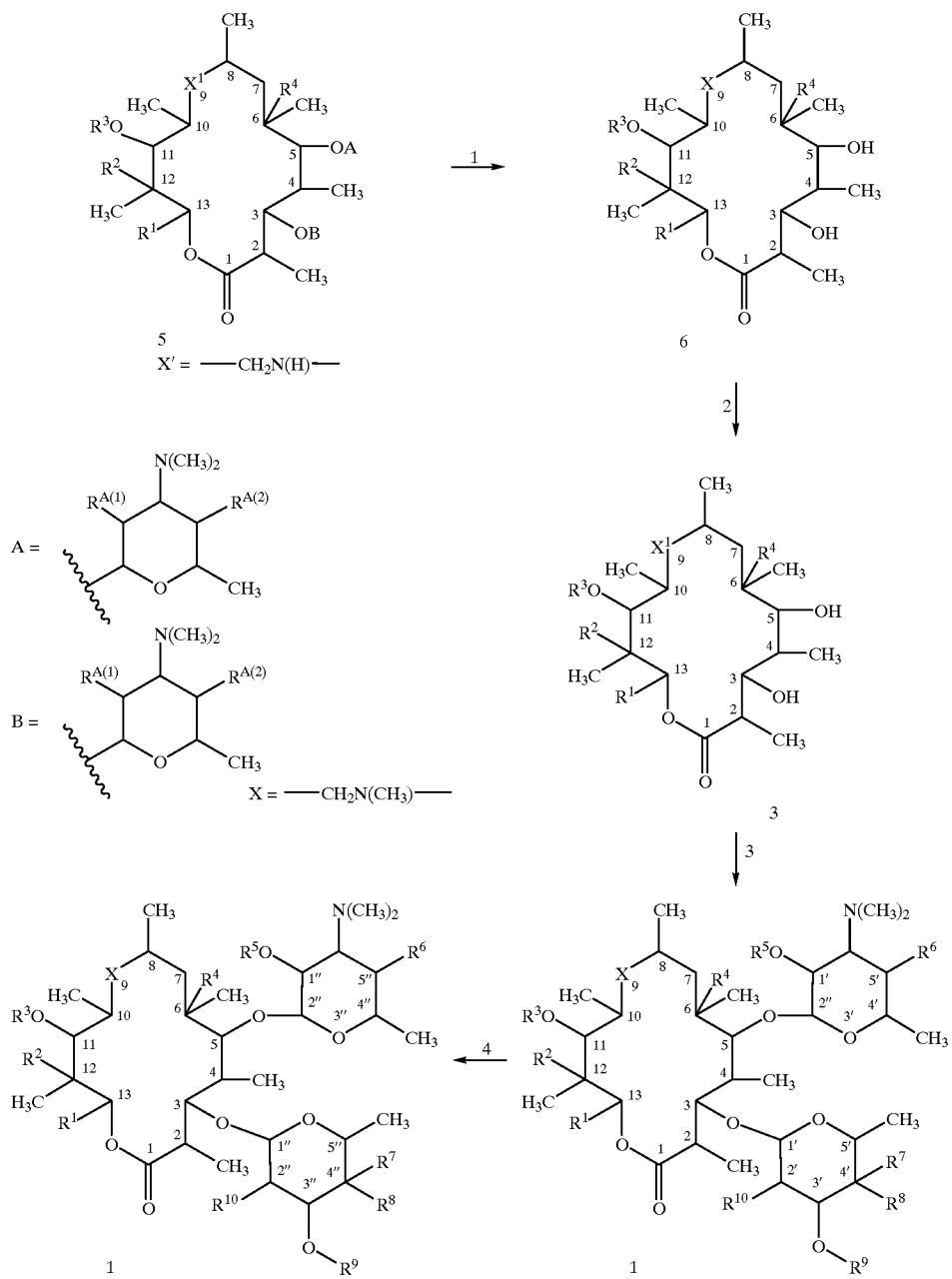

The compounds of the invention are readily prepared. Referring to Schemes 1–2, the starting compounds of Formulas 4 and 5 may be prepared according to one or more methods familiar to those skilled in the art including the synthetic methods described by U.S. Pat. Nos. 4,474,768 and 4,517,359, both of which are hereby incorporated by reference. The methods described in International Application No. PCT/GB97/01810 filed Jul. 4, 1997 (Peter Francis Leadlay, James Staunton, Jesus Cortes and Michael Stephen Pacey), and International Application No. PCT/GB97/01819 filed Jul. 4, 1997 (Peter Francis Leadlay, James Staunton, and Jesus Cortes), both of which are incorporated by reference, may also be used.

In step 1 of Scheme 1, the desosamine or desosamine derivative A and the cladinose or cladinose derivative B are cleaved from the starting compound of Formula 4 using one or more methods known to those skilled in the art to provide a compound of Formula 3. Particularly suitable methods are described by Djokic, S., et al., *J. Chem. Res.* (S), 1988:152–153; LeMahieu, R. A., et al., *J. Med. Chem.*, 17(9):953–956 (1974); Jones, A. B., Tet. Letters, 34(31):4913–4916 (1993); and Djokic, S., et al., *J. Chem. Soc. Perkin Trans. I*, 1986:1881–1890.

The cleavage of the sugars A and B forms an aglycone compound of Formula 3. Step 1 also encompasses optional purification and isolation procedures known to those skilled in the art, including, for example, preparatory high performance liquid chromatography (HPLC).

In step 2 of Scheme 1, the compound of Formula 3 is contacted with a biological culture to form a compound of Formula 2. Unexpectedly, it has been found that blocked mutants of oleandomycin producing strains of *Streptomyces antibioticus*, which have heretofore been thought to act only upon naturally occurring macrolides, are capable of attaching oleandrose to azalide aglycone compounds. A particularly useful strain for this biotransformation is *Streptomyces antibioticus* ATCC 202189, which is a strain of *Streptomyces antibioticus* that was deposited in accordance with the terms of the Budapest Treaty with the American Type Culture Collection; 12301 Parklawn Drive, Rockville, Md. 20852, U.S.A., on Jan. 13, 1999, and has the accession number ATCC 202189. *Streptomyces antibioticus* ATCC 202189 is a redeposit of *Streptomyces antibioticus* ATCC 31771, which is described by Spagnoli, R., et al., *J. Antibiot.*, 36(4): 365–75 (1983). Reaction and fermentation conditions suitable for the growth of these strains and the formation of compounds of Formula 2 are known to those skilled in the art and are described, for example, by Weber, J. M., et al., *J. Bacteriol.*, 164(1):425–433 (1985). Isolation and purification steps are also described therein.

Other suitable bacteria that may be used in step 2 include blocked mutants of *Saccharopolyspora erythraea* strains comprising at least one eryCIV or eryBIII mutation, or a mixture of at least one eryCIV and at least one eryBIII mutation. The preparation of mutants suitable for the invention is described by Salah-Bey, K., et al., Mol. Gen. Genet., 257: 542–553 (1998); Gaisser, S., et al., *Mol. Gen. Genet.*, 258:78–88 (1998); and Hopwood, D. A., et al., *Genetic Manipulations of Streptomyces A Laboratory Manual*. 39–40 (1985). Blocked mutants of erythromycin producing strains of *Saccharopolyspora erythraea* have unexpectedly been found to be capable of attaching cladinose to macrolide aglycone compounds. A particularly useful strain for this biotransformation is *Saccharopolyspora erythraea* ATCC 202199, which is a strain of *Saccharopolyspora erythraea* that was deposited in accordance with the terms of the Budapest Treaty with the American Type Culture Collection; 12301 Parklawn Drive, Rockville, Md. 20852, U.S.A., on Jan. 22, 1999, and has the accession number ATCC 202199. *Saccharopolyspora erythraea* ATCC 202199 is described by Weber, J. M., et al., *J. Bacteriol.*, 164(1):425–433 (1985).

The use of *Streptomyces antibioticus* ATCC 202189 provides a compound of Formula 2 wherein $R^6$, $R^9$, and $R^{10}$ is each hydrogen. The use of *Saccharopolyspora erythraea* strains comprising at least one eryCIV or eryBIII mutation provide, for example, compounds of Formula 2 wherein $R^6$ is H or OH and $R^9$ and $R^{10}$ is independently H or $CH_3$.

Following the isolation of the compound of Formula 2, chemical reactions known to those skilled in the art may be used to form the final product of Formula 1. Suitable chemical reactions are described, for example, by: U.S. Pat. Nos. 4,474,768 and 4,517,359, both of which are incorporated herein in their entirety; U.S. Provisional Patent Application Nos.: 60/063,676, filed Oct. 29, 1997 (Yong-Jin Wu); 60/063,161, filed Oct. 29, 1997 (Yong-Jin Wu); 60/054,866, filed Aug. 6, 1997 (Hiroko Masamune, Yong-Jin Wu, Takushi Kaneko and Paul R. McGuirk); 60/049,980, filed Jun. 11, 1997 (Brian S. Bronk, Michael A. Letavic, Takushi Kaneko and Bingwei V. Yang); 60/049,348, filed Jun. 11, 1997 (Brian S. Bronk, Hengmiao Cheng, E. A. Glazer, Michael A. Letavic, Takushi Kaneko and Bingwei V. Yang); 60/070,358, filed Jan. 2, 1998 (Yong-Jin Wu); 60/070,343, filed Jan. 2, 1998 (Diriam); and 60/097,075, filed Aug. 19, 1998 (Hengmiao Cheng, Michael A. Letavic, Carl B. Ziegler, Jason K. Dutra, Brian S. Bronk), all of which are incorporated by reference in their entirety; and PCT Application Nos.: PCT/IB98/00839, filed May 29, 1998 (Brian S. Bronk, Hengmiao Cheng, E. A. Glazer, Michael A. Letavic, Takushi Kaneko and Bingwei V. Yang); PCT/GB97/01810 filed Jul. 4, 1997 (Peter Francis Leadlay, James Staunton, Jesus Cortes and Michael Stephen Pacey); and PCT/GB97/01819 filed Jul. 4, 1997 (Peter Francis Leadlay, James Staunton and Jesus Cortes), all of which are incorporated by reference in their entirety; and European Patent Application Nos.: 180415, filed Oct. 24, 1985; 195960, filed Mar. 5, 1986; and 422843, filed Oct. 4, 1996, all of which are incorporated by reference in their entirety.

Synthesis of the compounds of this invention may comprise other steps in addition to those shown in Scheme 1. For example, groups bonded to the azalide aglycone (i.e., $R^a$ bound to X, $R^1$, $R^2$, $R^3$ and $R^4$) may be modified following cleavage of one or both sugars from the starting material of Formula 3. Scheme 2 provides an example of a modification of the azalide aglycone.

According to Scheme 2, both sugars bonded to the starting compound of Formula 5 are cleaved in step 1 to form the aglycone compound of Formula 6. In step 2, the hydrogen bonded to the nitrogen atom of X' is converted to a methyl group using methods well known to those skilled in the art. This reaction yields a compound of Formula 3, which is then contacted with a biological culture in step 3 according to the biotransformation method described above to form a compound of Formula 2. This compound, which itself may exhibit desirable pharmacological activity, may be isolated and purified, or may undergo further reaction to yield a compound of Formula 1.

Because of their general applicability, Schemes 1 and 2 do not represent the stereochemistries of particular starting materials, intermediates or final products. It is to be understood, however, that the compounds of the invention may have asymmetric carbon atoms and therefore exist in different enantiomeric and diastereomeric forms. Diastereomeric mixtures can be separated into their individual diastereomers by methods known to those skilled in the art. These include, for example, chromatography and fractional crystallization. Enantiomers may be separated by converting enantiomeric mixtures into diastereomeric mixtures by reaction with an appropriate optically active compound (e.g., alcohol), separating the diastereomers and converting (e.g., hydrolyzing) the individual diastereomers to the corresponding pure enantiomers. See, e.g., Jacques, J., et al., *Enantiomers, Racemates and Resolutions*, (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed. Univ. of Notre Dame Press, Notre Dame, Ind., 1972). Separation of enantiomers may also be accomplished using chiral chromatography. All isomers, including diastereomer mixtures and pure enantiomers, are considered to be part of the invention.

The compounds of the invention that are basic in nature are capable of forming a wide variety of different salts with various inorganic and organic acids. Although such salts must be pharmaceutically acceptable in order to be administered to mammals, fish or birds, it is often desirable to initially isolate compounds of the invention from reaction mixtures as pharmaceutically unacceptable salts, which are then converted back to the free base compounds by treatment with an alkaline reagent, and subsequently converted to pharmaceutically acceptable acid addition salts. The acid addition salts of the basic compounds of this invention are readily prepared by treating the compounds with substantially equivalent amounts of chosen mineral or organic acids in aqueous solvent mediums, or in suitable organic solvents such as methanol and ethanol. Upon careful evaporation of these solvents, the desired solid salts are readily obtained. Desired salts can also be precipitated from solutions of the free base compound in organic solvents by adding to the solutions appropriate mineral or organic acids.

Those compounds of the invention that are acidic in nature are capable of forming base salts with various cations. As above, when a pharmaceutically acceptable salt is required, it may be desirable to initially isolate a compound of the invention from a reaction mixture as a pharmaceutically unacceptable salt, which can then be converted to a pharmaceutically acceptable salt in a process analogous to that described above. Examples of base salts include alkali metal or alkaline-earth metal salts and particularly sodium, amine and potassium salts. These salts are all prepared by conventional techniques. The chemical bases used to prepare the pharmaceutically acceptable base salts of this invention are those which form non-toxic base salts with the acidic compounds of the invention. Such non-toxic base salts include those derived from pharmacologically acceptable cations such as sodium, potassium, calcium, magnesium, and various amine cations. These salts can easily be prepared by treating the corresponding acidic compounds with an aqueous solution containing the desired pharmacologically acceptable bases and then evaporating the resulting solution to dryness, preferably under reduced pressure. They may also be prepared by mixing lower alkanolic solutions to dryness in the same manner as before. In either case, stoichiometric quantities of reagents are preferably employed in order to ensure completeness of reaction and maximum yields of the desired final product.

ASSAYS

The antibacterial and antiprotozoa activity of the compounds of the invention against bacterial and protozoa pathogens is demonstrated by their ability to inhibit growth of defined strains of human (Assay 1) or animal (Assays 2 and 3) pathogens. Assay 2 is utilized to test for activity against *Pasteurella multocida* and Assay 3 is utilized to test for activity against *Pasteurella haemolytica*. These assays may also provide insight into the anticancer activity of the compounds of the invention.

Assay 1

Assay 1, described below, employs conventional methodology and interpretation criteria and is designed to provide direction for chemical modifications that may lead to compounds that circumvent defined mechanisms of macrolide resistance. In Assay 1, a panel of bacterial strains is assembled to include a variety of target pathogenic species, including representatives of macrolide resistance mechanisms that have been characterized. Use of this panel enables chemical structure/activity relationships to be determined with respect to potency, spectrum of activity, and structural elements or modifications that may be necessary to obviate resistance mechanisms. Bacterial pathogens used in the screening panel are shown in the table below.

| Strain Designation | Macrolide Resistance Mechanism(s) |
|---|---|
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | erythromcycin intermediate resistance |
| *Escherichia coli* 0266 | susceptible |

In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally preventing the binding of all three structural classes. Two types of macrolide efflux have been described; msrA encodes a component of an efflux system in staphylococci that prevents the accumulation of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in Stutcliffe, J., et al., "Detection of Erythromycin-Resistant Determinants By PCR", Antimicrobial Agents and Chemotherapy, 40(1):2562–2566 (1996). The assay is performed in microtiter trays and interpreted according to *Performance Standards for Antimicrobial Disk Susceptibility Tests—Sixth Edition; Approved Standard,* published by the National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

Assay 2

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 $\mu$l of DMSO. Dilutions of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a 10 cell suspension per 200 $\mu$l. The BHI cell suspensions are mixed with respective serial dilutions of the test compound, and incubated at 37EC for 18 hours. The minimum inhibitory concentration (MIC) is equal to the concentration of the compound exhibiting 100% inhibition of growth of P. multocida as determined by comparison with an uninoculated control.

Assay 3

This assay is based on the agar dilution method using a Steers Replicator. Two to five colonies isolated from an agar plate are inoculated into BHI broth and incubated overnight at 37EC with shaking (200 rpm). The next morning, 300 µl of the fully grown P. haemolytica preculture is inoculated into 3 ml of fresh BHI broth and is incubated at 37EC with shaking (200 rpm). The appropriate amounts of the test compounds are dissolved in ethanol and a series of two-fold serial dilutions are prepared. Two ml of the respective serial dilution is mixed with 18 ml of molten GHI agar and solidified. When the inoculated P. haemolytica culture reaches 0.5 McFarland standard density, about 5 µl of the P. haemolytica culture is inoculated onto BHI agar plates containing the various concentrations of the test compound using a Steers Replicator and incubated for 18 hours at 37EC. Initial concentrations of the test compound range from 100–200 µg/ml. The MIC is equal to the concentration of the test compound exhibiting 100% inhibition of growth of P. haemolytica as determined by comparison with an uninoculated control.

The in vivo activity of the compounds of Formula 1 can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3 \times 10^3$ CFU/ml bacterial suspension (P. Multocida strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck, whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The P. multocida model monitoring continues for 96 hours (four days) post challenge.

The $PD_{50}$ is a calculated dose at which the compound tested protects 50% of a group of mice from mortality due to the bacterial infection which would be lethal in the absence of drug treatment.

PHARMACEUTICAL FORMATIONS AND METHODS OF TREATMENT

The compounds of this invention (hereinafter also referred to as "the active compounds"), may be administered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to the active compound, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. Moreover, oral pharmaceutical compositions can be suitably sweetened and/or flavored. In general, the active compounds are present in such dosage forms at concentration levels ranging from about 5.0% to about 70% by weight.

For oral administration, tables containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

In addition to the common dosage forms set out above, the compounds of the invention may also be administered by controlled release means and/or delivery devices capable of releasing the active compound at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

Examples of controlled release pharmaceutical compositions and delivery devices that may be adapted for the administration of the active compounds of the invention are described in U.S. Pat. Nos. 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are hereby incorporated by reference.

For parenteral administration, solutions of an active compound in either sesame or peanut oil or in aqueous propylene glycol may be employed. The aqueous solutions should be suitably buffered (preferably pH greater than 8) if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds of the invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsion caprolactone, polyhydroxy butyric acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following examples further illustrate the methods, intermediates and compounds of the invention. It is to be understood that this invention is not limited to the specific details of the examples provided below.

EXAMPLES

All NMR spectra were measured in CDCl$_3$ using a Bruker 500 MHz DMX spectrometer. Peak positions are expressed in parts per million (ppm) downfield from tetramethylsilane (TMS). The atom number shown in the NMR structure is not representative of standard nomenclature, but correlates NMR data to that particular example. HPLC-MS data was acquired using a Hewlett-Packard 1050 liquid chromatograph interfaced to a VG Platform II mass spectrometer equipped with an APCI source (method A) or using a Hewlett-Packard 1100 series LC-MSD system equipped with an APCI source (method B).

| HPLC method B: | |
|---|---|
| Column | Phenomenex Prodigy 5 µm C8 3.2 mm = 250 mm |
| Flow | 0.5 mL/min |
| Mobile phase | Gradient: acetonitrile-0.1% trifluoroacetic acid (15–85) to acetonitrile-0.1% trifluoroacetic acid (25–75) over 50 minutes |

Example 1

Preparation of 3-O-oleandrosyl-5-O-desosaminyl-azithromydin using *Streptomyces antibioticus* ATCC 202189

The culture *Streptomyces antibioticus* ATCC 202189 was inoculated as a patch onto an agar medium composed of (per liter): Difco yeast extract, 10 g; Difco Bacto peptone, 10 g; dextrose, 5 g; MOPS, 10 g; Bacto agar, 17 g; pH adjusted to 7.0. The culture was incubated at 28° C. for 5 days. After 5 days, a 6 mm plug of the patch culture was inoculated into 500 ml Erlenmeyer flasks containing 50 ml of the seed medium composed of (per liter): dextrose, 15 g; nutrisoy flour, 30 g; MgSO$_4$×7H$_2$O, 1 g; Difco yeast extract, 1 g; CaCO$_3$, 10 g; soybean oil, 6 g; pH adjusted to 7.0. The seed cultures were incubated with 225 rpm agitation at 29° C. for 24 hours. After 24 hours, 1.5 ml of the seed culture was inoculated into the second stage seed in 500 ml Erlenmeyer flasks containing 50 ml of the seed medium described above. The second stage seed culture was incubated with 225 rpm agitation at 29° C. for 24 hours. After 24 hours, 114 ml of the second stage seed culture was inoculated into each of two 5 liter fermentors containing 3.8 liters of fermentation medium composed of (per liter): dextrose, 50 g; nutrisoy flour, 20 g; corn meal, 3 g; Difco yeast extract, 2 g; CaCO$_3$, 20 g; P2000 antifoam, 0.5 ml; pH adjusted to 7.0. The fermentors were incubated at 29° C., 400 rpm, with an aeration rate of 3 liters per minute for a total of 120 hours. At 48 hours, 38 ml of a 50 mg/ml solution of the azithromycin aglycone (prepared according to the method of Djokic, S., et al., *J. Chem. Res. Synop.*, 5:152–153 (1988)) dissolved in methanol was added aseptically to each of the two fermentors. After 120 hours total incubation time, the fermentors were harvested. The whole broth was clarified by centrifugation, the pH of the supernatant was adjusted to 9.5 with sodium hydroxide, and the supernatant was extracted three times with 3.5 liters of ethyl acetate. The ethyl acetate extract was concentrated in vacuo to an oil (approximately 5 grams).

1.88 grams of this oil was dissolved in 75 ml of 1 molar pH 3 sodium phosphate dibasic buffer, the pH was adjusted to 2 with phosphoric acid. The solution was washed with 75 ml of ethyl acetate, pH adjusted to 9 with sodium hydroxide solution and the compound extracted with three 150 ml portions of chloroform. The chloroform extracts were combined and the solvent removed in vacuo yielding 1.16 grams brown solid. 76 mg of this material was purified by reverse phase HPLC using a Luna C8(2) column (21.2×250 mm) with a mobile phase gradient of (0.1% aqueous trifluroacetic acid)acetonitrile 85-15 to 75-25 over 50 minutes at a flow rate of 20 ml/min. Fractions containing the product of interest (22–35 minutes) were combined, saturated with sodium bicarbonate and extracted with three portions methylene chloride. The methylene chloride extracts were combined, dried over sodium sulfate, filtered and evaporated in vacuo yielding 29 mg of material. This material was further purified by reverse phase HPLC using a Luna(2) C8 column (21.2×250 mm) with a mobile phase gradient of (0.1% aqueous trifluroacetic acid)-(acetonitrile-tetrahydrofuran 4-1) 90-10 to 70-30 over 100 minutes at a flow rate of 20 ml/min. Fractions containing the product of interest (37–44 minutes) were combined, saturated with sodium bicarbonate and extracted with three portions methylene chloride. The methylene chloride extracts were combined, dried over sodium sulfate, filtered and evaporated in vacuo yielding 8 mg of above-titled compound. The structure was confirmed by MS and NMR.

HPLC retention time—Method B—26.6 minutes.

APCI-MS-(M+H)$^+$ observed at m/z 735, required for $C_{37}H_{71}N_2O_{12}$-735.

NMR data as follows:

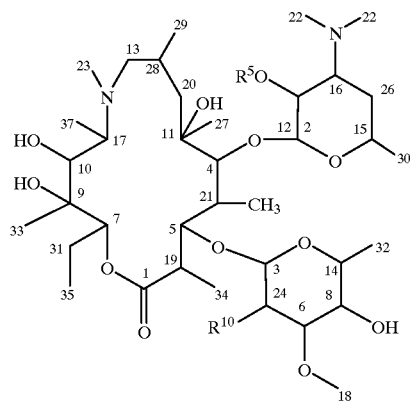

| # | $^{13}$C-ppm | # attached $^1$H | $^1$H-ppm |
|---|---|---|---|
| 1 | 179.08 | 0 | |
| 2 | 104.17 | 1 | 4.38 |
| 3 | 96.86 | 1 | 5.33 |
| 4 | 84.99 | 1 | 3.70 |
| 5 | 79.57 | 1 | 4.33 |
| 6 | 78.78 | 1 | 3.52 |
| 7 | 78.07 | 1 | 4.74 |
| 8 | 75.79 | 1 | 3.24 |
| 9 | 74.72 | 0 | |
| 10 | 74.55 | 1 | 3.72 |
| 11 | 74.09 | 0 | |
| 12 | 71.39 | 1 | 3.30 |
| 13 | 70.57 | 2 | 2.56/2.07 |
| 14 | 69.59 | 1 | 3.96 |
| 15 | 69.45 | 1 | 3.65 |
| 16 | 65.92 | 1 | 2.58 |
| 17 | 62.71 | 1 | 2.76 |
| 18 | 56.70 | 3 | 3.45 |
| 19 | 45.72 | 1 | 2.86 |
| 20 | 42.94 | 2 | 1.87/1.34 |
| 21 | 41.81 | 1 | 2.06 |
| 22 | 40.80 | 3 | 2.34 |
| 23 | 36.82 | 3 | 2.38 |
| 24 | 33.6 | 2 | 2.36/1.63 |
| 26 | 29.28 | 2 | 1.72/1.30 |
| 27 | 27.87 | 3 | 1.38 |
| 28 | 27.21 | 1 | 2.04 |
| 29 | 22.39 | 3 | 0.96 |
| 30 | 21.89 | 3 | 1.27 |
| 31 | 21.56 | 2 | 1.95/1.55 |
| 32 | 18.32 | 3 | 1.41 |
| 33 | 16.62 | 3 | 1.14 |
| s34 | 15.52 | 3 | 1.27 |
| 35 | 11.65 | 3 | 0.94 |
| 36 | 9.52 | 3 | 1.11 |
| 37 | 7.93 | 3 | 1.15 |

Example 2

Preparation of 3-O-oleandrosyl-5-O-desosaminyl-N-desmethyl-azithromycin using *Streptomyces antibioticus* ATCC 202189

The culture *Streptomyces antibioticus* ATCC 202189 was inoculated as a patch onto an agar medium composed of (per liter): Difco yeast extract, 10 g; Difco Bacto peptone, 10 g; dextrose, 5 g; MOPS, 10 g; Bacto agar, 17 g; pH adjusted to 7.0. The culture was incubated at 28EC for 5 days. After 5 days, a 6 mm plug of the patch culture was inoculated into 500 ml Erlemeyer flasks containing 50 ml of the seed medium composed of (per liter): dextrose, 15 g; nutrisoy flour, 30 g; $MgSO_4C7H_2O$, 1 g; Difco yeast extract, 1 g; $CaCO_3$, 10 g; soybean oil, 6 g; pH adjusted to 7.0. The seed cultures were incubated with 225 rpm agitation at 29EC for 24 hours. After 24 hours, 1.5 ml of the seed culture was inoculated into the second stage seed in 500 ml Erlenmeyer flasks containing 50 ml of the seed medium described above. The second stage seed culture was incubated with 225 rpm agitation at 29EC for 24 hours. After 24 hours 60 ml of the second stage seed culture was inoculated into each of two fermentors containing 2 liters of fermentation medium composed of (per liter): dextrose, 50 g; nutrisoy flour, 20 g; corn meal, 3 g; Difco yeast extract, 2 g; $CaCO_3$, 20 g; P2000 antifoam, 0.5 ml; pH adjusted to 7.0. The fermentors were incubated at 29EC, 400 rpm, with an aeration rate of 2 liters per minute for a total of 120 hours. Ten milliliters of a 50 mg/ml solution of the N-desmethyl-azithromycin aglycone dissolved in methanol was added aseptically to one of the fermentors at 24 and 48 hours. Nineteen milliliters of a 50 mg/ml solution of the N-desmethyl-azithromycin aglycone dissolved in methanol was added aseptically to the second fermentor at 48 hours. After 120 hours total incubation time, the fermentors were harvested. The whole broth was clarified by centrifugation, the pH of the supernatant was adjusted to 9.5 with sodium hydroxides, and the supernatant was extracted three times with 7.3 liters of ethyl acetate. The ethyl acetate extract was concentrated to 20 ml using a Büchi rotary evaporator followed by concentrating to an oil in vacuo. This material was dissolved in 25 ml of methylene chloride and the product was extracted into 50 ml of 1M sodium phosphate dibasic buffer at pH 3. The lower layer was removed, the aqueous layer was adjusted to pH 8.5 with sodium bicarbonate and the desired material was extracted with three 100 ml portions methylene chloride. The methylene chloride portions were combined, dried over sodium sulfate, filtered, and the solvent removed in vacuo to yield 1.03 grams brown solid. 100 mg of this material was purified by reverse phase HPLC using a Prodigy C8 column (21.2× 250 mm) with a mobile phase gradient of (0.1% aqueous trifluroacetic acid)-acetonitrile 90-10 to 80-20 over 75 minutes at a flow rate of 20 ml/min. Fractions containing the product of interest (59–69 minutes) were combined, the pH adjusted to 8.5 with sodium bicarbonate and the desired product extracted with two portions of methylene chloride. The methylene chloride extracts were combined, dried over sodium sulfate, filtered and solvent removed in vacuo to yield 4 mg of the above-titled compound. The structure was confirmed by MS and NMR.

HPLC retention time—Method B—26.5 minutes.

APCI-MS-(M+H)+ observed at m/z 721, required for $C_{36}H_{69}N_2O_{12}$-721.

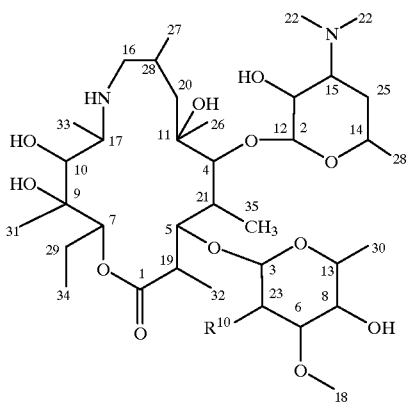

| # | $^{13}$C-ppm | #H | $^1$H-ppm |
|---|---|---|---|
| 1 | 178.36 | 0 | |
| 2 | 104.35 | 1 | 4.37 |
| 3 | 97.45 | 1 | 5.26 |
| 4 | 85.14 | 1 | 3.71 |
| 5 | 79.92 | 1 | 4.40 |
| 6 | 78.67 | 1 | 3.52 |
| 7 | 78.51 | 1 | 4.78 |
| 8 | 75.61 | 1 | 3.25 |
| 9 | 74.32 | 0 | |
| 10 | 74.06 | 0 | |
| 11 | 73.76 | 1 | 3.54 |
| 12 | 70.99 | 1 | 3.30 |
| 13 | 69.47 | 1 | 3.96 |
| 14 | 69.36 | 1 | 3.64 |
| 15 | 65.79 | 1 | 2.52 |
| 16 | 57.35 | 2 | 3.09/1.90 |
| 17 | 56.99 | 1 | 2.67 |
| 18 | 56.58 | 3 | 3.45 |
| 19 | 45.54 | 1 | 2.86 |
| 20 | 42.88 | 2 | 1.91/1.47 |
| 21 | 41.64 | 1 | 2.04 |
| 22 | 40.72 | 3 | 2.35 |
| 23 | 33.69 | 2 | 2.36/1.61 |
| 24 | 30.08 | 1 | 1.80 |
| 25 | 29.29 | 2 | 1.71/1.28 |
| 26 | 27.70 | 3 | 1.36 |
| 27 | 22.19 | 3 | 1.00 |
| 28 | 21.76 | 3 | 1.26 |
| 29 | 21.29 | 2 | 1.93/1.56 |
| 30 | 18.30 | 3 | 1.40 |
| 31 | 16.49 | 3 | 1.13 |
| 32 | 15.67 | 3 | 1.29 |
| 33 | 14.43 | 3 | 1.20 |
| 34 | 11.54 | 3 | 0.95 |
| 35 | 9.70 | 3 | 1.12 |

Example 3

Preparation of 6-deoxy-azithromycin 6,7-anhydro-azithromycin was produced according to the procedure described by Jones, A. B., et al., *Tetrahedron Lett.*, 34(31): 4913–16 (1993). 2 grams of this compound and 1.24 grams of PtO (Aldrich) were dissolved in 100 ml acetic acid and placed in Parr shaker under 40 psi hydrogen. After 70 hours, the solution was filtered, diluted with water, and adjusted to pH 8.5 with sodium bicarbonate and ammonium hydroxide. The product was extracted with methylene chloride and the methylene chloride was removed in vacuo. Additional product was obtained from a second run using a process like that above. The yields of the two runs were combined to provide a total of 3.45 grams of 6-deoxy-azithromycin from 3.75 grams of 6,7-anhydro-azithromycin. The structure was confirmed by MS.

APCI-MS-(M+H)+ observed at m/z 733, required for $C_{38}H_{73}N_2O_{11}$-733.

Example 4

Preparation of the 6-deoxy-azithromycin aglycone 2.7 grams of 6-deoxy-azithromycin was stirred in 50 ml chloroform and 100 ml 6 molar hydrochloric acid for 5 hours at ambient temperature, 1.5 hours at 80EC, and 4 hours at ambient temperature. The aqueous layer was separated and the pH adjusted to 9 with sodium bicarbonate and ammonium hydroxide. The compound was extracted with methylene chloride, the solution dried over sodium sulfate, filtered and solvent removed in vacuo yielding 1.52 grams. 1.2 grams of this material was purified by reverse phase HPLC on an Inertsil C8 column (50×250 mm) using a gradient mobile phase of (0.1% aqueous trifluroacetic acid)—ACN 100-0 to 75-25 over 50 minutes at a flow rate of 125 ml/min. Fractions containing the product of interest (35–39 minutes) were combined, saturated with sodium bicarbonate and extracted with methylene chloride. The methylene chloride was separated, dried over sodium sulfate, filtered and evaporated in vacuo yielding 0.33 grams of above-titled compound. The structure was confirmed by MS.

HPLC retention time—Method B—16.8 minutes.

APCI-MS-(M+H)+ observed at m/z 418, required for $C_{22}H_{44}NO_6$-418.

Example 5

Preparation of 3-O-oleandrosyl-5-O-desosaminyl-6-deoxy-azithromycin using *Streptomyces antibioticus* ATCC 202189

The culture *Streptomyces antibioticus* ATCC 202189 was inoculated as a patch onto an agar medium composed of (per liter): Difco yeast extract, 10 g; Difco Bacto peptone, 10 g; dextrose, 5 g; MOPS, 10 g; Bacto agar, 17 g; pH adjusted to 7.0. The culture was incubated at 28° C. for 5 days. After 5 days, a 6 mm plug of the patch culture was inoculated into 500 ml Erlenmeyer flasks containing 50 ml of the seed medium composed of (per liter): dextrose, 15 g; nutrisoy flour, 30 g; $MgSO_4C7H_2O$, 1 g; Difco yeast extract, 1 g; $CaCO_3$, 10 g; soybean oil, 6 g; pH adjusted to 7.0. The seed cultures were incubated with 225 rpm agitation at 29° C. for 24 hours. After 24 hours, 1.5 ml of the seed culture was inoculated into the second stage seed in 500 ml Erlenmeyer flasks containing 50 ml of the seed medium described above. The second stage seed culture was incubated with 225 rpm agitation at 29° C. for 24 hours. After 24 hours 0.9 ml of the second stage seed culture was inoculated into each of forty 250 ml Erlenmeyer flasks containing 30 ml of fermentation medium composed of (per liter): dextrose, 50 g; nutrisoy flour, 20 g; corn meal, 3 g; Difco yeast extract, 2 g; $CaCO_3$, 20 g; pH adjusted to 7.0. The flasks were incubated at 29° C., 225 rpm, for a total of 112 hours. At 24 and 48 hours, 0.25 ml of a 25 mg/ml solution of the 6-deoxy-azithromycin aglycone dissolved in DMSO was added aseptically to each of the flasks. After 112 hours total incubation time, the flasks were harvested. The whole broth was clarified by centrifugation, the pH of the supernatant was adjusted to 9.5 with sodium hydroxide, and the supernatant was extracted three times with 300 ml of ethyl acetate. The ethyl acetate extract was concentrated to 10 ml using a Büchi rotary evaporator followed by concentrating to an oil in vacuo. Assay using LC-MS method A showed a peak with a m/z of (M+H)$^+$ 719 corresponding to the predicted 3-O-oleandrosyl-5-O-desosaminyl-6-deoxy-azithromycin.

HPLC retention time—Method A—15.7 minutes.

APCI-MS-(M+H)$^+$ observed at m/z 719, required for $C_{37}H_{71}N_2O_{11}$-719.

Example 6

Preparation of 3-O-oleandrosyl-5-O-desosaminyl-6-deoxy-N-desmethyl-azithromycin

The feeding of 6-deoxy-N-desmethyl-azithromycin aglycone to the culture *Streptomyces antibioticus* ATCC 202189 produces 3-O-oleandrosyl-5-O-desosaminyl-6-deoxy-N-desmethyl-azithromycin. Fermentation and extraction procedures such as those described in Example 1 are easily adapted for this process.

Example 7

Preparation of azithromycin using *Saccharopolyspora erythraea* ATCC 202199

*Saccharopolyspora erythraea* ATCC 202199 was plated on petris containing ½YPD agar (0.25% dextrose, 0.5% Difco Yeast Extract, 0.5% Difco Bacto Peptone, 0.5% MOPS buffer, 1.7% Difco Bacto agar, pH adjusted to 7.0, autoclaved at 121° C., 25 minutes, cooled then poured) and incubated at 28° C. until well grown (5–8 days). Agar plugs were inoculated into 1×6 inch glass tubes with metal caps containing 6 ml ½YPD broth (0.25% dextrose, 0.5% Difco Yeast Extract, 0.5% Difco Bacto Peptone, 0.5% MOPS buffer, pH adjusted to 7.0, autoclaved at 121° C., 20 minutes) and two 5 mm diameter glass beads using sterile 6 mm diameter transfer pipets. Tubes were incubated at 29° C., 225 rpm, 4° incline for 48 hours. 0.4 ml was then transferred into 1×6 inch glass tubes with metal caps containing 4 ml Ery-P medium (5% dextrose, 3% Nutrisoy flour, 0.3% ammonium sulfate, 0.5% sodium chloride, 0.6% calcium carbonate, pH adjusted to 7.0, autoclaved at 121° C., 20 minutes) and incubated at 29° C., 225 rpm, 4° incline for three or four days. Azithromycin agylcone (prepared according to Djokic, S., et al., *J. Chem. Res. Synop.*, 5:152–153 (1988)) was added to these tubes at 24 hours into the fermentation (15 mg/ml methanol stock solution) to a final concentration of 0.1 mg/ml. Samples were assayed using *Micrococcus luteus* ATCC 9341 as an indicator organism as well as by thin layer chromatography (TLC). A biotransformation product was generated which co-migrated with azithromycin (assayed by TLC) and was bioactive against *M. luteus* ATCC 9341. Accordingly, the product was azithromycin.

Example 8

Preparation of clarithromycin oxime 660 mg of clarithromycin oxime (prepared from clarithromycin according to the method disclosed by EP 0180415, which is incorporated herein by reference) was dissolved in HF-pyridine solution (70-30 from Aldrich) and stirred at room temperature for 40 minutes. The reaction mixture was poured into a cold solution of saturated sodium bicarbonate. The desired product was extracted with chloroform and the chloroform removed in vacuo to yield a yellowish residue. The structure was confirmed by MS.

APCI-MS-(M+H)$^+$ observed at m/z 448, required for $C_{22}H_{42}NO_8$-448.

Example 9

Preparation of clarithromycin oxime aglycone

The entire amount of clarithromycin oxime prepared according to Example 8 was dissolved in 50 ml of ethanol-:water (32:48); 358 mg of sodium bicarbonate was then added and the solution heated to 85° C. overnight. The solvent was removed in vacuo and the residue was dissolved in aqueous saturated sodium bicarbonate and chloroform. The lower layer was removed and the chloroform was removed in vacuo. The resulting material was purified by silica column chromatography using acetone:hexane (20:80) to yield 169 mg of product. The structure was confirmed by MS.

APCI-MS-(M+H)$^+$ observed at m/z 433, required for $C_{22}H_{41}O_8$-433.

Example 10

Preparation of clarithromycin using *Saccharopolyspora erythraea* ATCC 202199

*Saccharopolyspora erythraea* ATCC 202199 was plated on petris containing ½YPD agar (0.25% dextrose, 0.5% Difco Yeast Extract, 0.5% Difco Bacto Peptone, 0.5% MOPS buffer, 1.7% Difco Bacto agar, pH adjusted to 7.0, autoclaved at 121° C., 25 minutes, cooled then poured) and incubated at 28° C. until well grown (5–8 days). Agar plugs were inoculated into 1×6 inch glass tubes with metal caps containing 6 ml ½YPD broth (0.25% dextrose, 0.5% Difco Yeast Extract, 0.5% Difco Bacto Peptone, 0.5% MOPS buffer, pH adjusted to 7.0, autoclaved at 121° C., 20 minutes) and two 5 mm diameter glass beads using sterile 6 mm diameter transfer pipets. Tubes were incubated at 29° C., 225 rpm, 4° incline for 48 hours. 0.4 ml was then transferred into 1×6 inch glass tubes with metal caps containing 4 ml Ery-P medium (5% dextrose, 3% Nutrisoy flour, 0.3% ammonium sulfate, 0.5% sodium chloride, 0.6% calcium carbonate, pH adjusted to 7.0, autodaved at 121° C., 20 minutes) and incubated at 29° C., 225 rpm, 4° incline for three or four days. At 24 hours into the fermentation, 6-methoxyerythronolide A was added to these tubes (15 mg/ml methanol stock solution) to a final concentration of 0.1 mg/ml. Samples were assayed using *Micrococcus luteus* ATCC 9341 as an indicator organism as well as by TLC. A biotransformation product was generated which was bioactive against *M. luteus* ATCC 9341 (TLC/Bioassay). Accordingly, the product was clarithromycin.

Example 11

Generation of a Blocked Mutant of a *Saccharopolyspora erythraea* eryCIV Mutant

A strain of *S. erythraea* is generated with a chromosomal mutation in the eryCIV gene following protocols established in the literature (Salah-Bey, K., et al., *Mol. Gen. Genet.*, 257: 542–553 (1998)). This strain is subsequently mutated by UV light or by chemical means using previously described methods. See, e.g., Hopwood, D. A., et al., *Genetic Manipulations of Streptomyces A Laboratory Manual.* 39–40 (1985). Mutated cells are screened on agar with a suitable indicator organism to select strains lacking antibiotic activity. Such strains are tested in agar co-synthesis experiments to select mutants that are blocked in aglycone formation and yet are still capable of glycosylation. Testing is done according to the protocol described by Spagnoli, R., et al., *J. Antibiot.*, 36(4): 365–75 (1983).

Example 12

Generation of a Blocked Mutant of a *Saccharopolyspora erythraea* eryBIII Mutant A strain of *S. erythraea* is generated with a chromosomal mutation in the eryBIII gene following protocols established by Gaisser, S., et al., *Mol. Gen. Genet.*, 258:78–88 (1998). This strain is subsequently mutated by UV light or by chemical means using previously described methods. See, e.g., Hopwood, D. A., et al., *Genetic Manipulations of Streptomyces A Laboratory Manual.* 39–40 (1985). Mutated cells are screened on agar with a suitable indicator organism to select strains lacking antibiotic activity. Such strains are tested in agar co-synthesis experiments to select mutants that are blocked in aglycone formation and yet are still capable of glycosylation. Testing is done according to the protocol described by Spagnoli, R., et al., *J. Antibiot.*, 36(4): 365–75 (1983).

Example 13

Generation of a Blocked Mutant of a *Saccharopolyspora erythraea* Strain with eryCIV and eryBIII Mutations A strain of *S. erythraea* is generated with a chromosomal mutation in both the eryCIV and the eryBIII genes following protocols established in the literature (Salah-Bey, K. et al. Mol. Gen. Genet. 1998. 257: 542–553; Gaisser, S. et al. *Mol. Gen. Genet.* 1998. 258: 78–88). This strain is subsequently mutated by UV light or by chemical means using previously described methods. See, e.g., Hopwood, D. A., et al., *Genetic Manipulations of Streptomyces A Laboratory Manual.* 39–40 (1985). Mutated cells are screened on agar with a suitable indicator organism to select strains lacking antibiotic activity. Such strains are tested in agar co-synthesis experiments to select mutants that are blocked in aglycone formation and yet are still capable of glycosylation. Testing is done according to the protocol described by Spagnoli, R., et al., *J. Antibiot.*, 36(4): 365–75 (1983).

Example 14

Preparation of 5-O-mycaminosyl-azithromycin using a blocked mutant of *Saccharopolyspora erythraea* (eryCIV)

The feeding of azithromycin agycone to a blocked mutant of *Saccharopolyspora erythraea* (eryCIV) produces 5-O-mycaminosyl-azithromycin. Fermentation and extraction procedures such as those described in Example 1 are easily adapted for this process.

Example 15

Preparation of 3"-desmethyl-azithromycin using a blocked mutant of *Saccharopolyspora erythraea* (eryBIII)

The feeding of azithromycin agycone to a blocked mutant of *Saccharopolyspora erythraea* (eryBIII) produces 3"-desmethyl-azithromycin. Fermentation and extraction procedures such as those described in Example 1 are easily adapted for this process.

Example 16

Preparation of 3"-desmethyl-5-O-mycaminosyl-azithromycin using a blocked mutant of *Saccharopolyspora erythraea* (eryBIII/eryCIV)

The feeding of azithromycin agycone to a blocked mutant of *Saccharopolyspora erythraea* (eryBIII/eryCIV) produces 3"-desmethyl-5-O-mycaminosyl-azithromycin. Fermentation and extraction procedures such as those described in Example 1 are easily adapted for this process.

Example 17

Preparation of 5-O-mycaminosyl-N-desmethyl-azithromycin using a blocked mutant of *Saccharopolyspora erythraea* (eryCIV)

The feeding of N-desmethyl-azithromycin agycone to a blocked mutant of *Saccharopolyspora erythraea* (eryCIV) produces 5-O-mycaminosyl-N-desmethyl-azithromycin. Fermentation and extraction procedures such as those described in Example 1 are easily adapted for this process.

Example 18

Preparation of 3"-desmethyl-N-desmethyl-azithromycin using a blocked mutant of *Saccharopolyspora erythraea* (eryBIII)

The feeding of N-desmethyl-azithromycin agycone to a blocked mutant of *Saccharopolyspora erythraea* (eryBIII) produces 3"-desmethyl-N-desmethyl-azithromycin. Fermentation and extraction procedures such as those described in Example 1 are easily adapted for this process.

Example 19

Preparation of 3"-desmethyl-5-O-mycaminosyl-N-desmethyl-azithromycin using a blocked mutant of *Saccharopolyspora erythraea* (eryBIII/eryCIV The feeding of N-desmethyl-azithromycin agycone to a blocked mutant of *Saccharopolyspora erythraea* (eryBIII/eryCIV produces 3"-desmethyl-5-O-mycaminosyl-N-desmethyl-azithromycin. Fermentation and extraction procedures such as those described in Example 1 are easily adapted for this process.

Example 20

Preparation of 5-O-mycaminosyl-6-deoxy-azithromycin using a blocked mutant of *Saccharopolyspora erythraea* (eryCIV)

The feeding of 6-deoxy-azithromycin agycone (Example 4) to a blocked mutant of *Saccharopolyspora erythraea* (eryCIV) produces 5-O-mycaminosyl-6-deoxy-azithromycin. Fermentation and extraction procedures such as those described in Example 1 are easily adapted for this process.

Example 21

Preparation of 3"-desmethyl-6-deoxy-azithromycin using a blocked mutant of *Saccharopolyspora erythraea* (eryBIII)

The feeding of 6-deoxy-azithromycin agycone (Example 4) to a blocked mutant of *Saccharopolyspora erythraea*

(eryBIII) produces 3"Y-desmethyl-6-deoxy-azithromycin. Fermentation and extraction procedures such as those described in Example 1 are easily adapted for this process.

Example 22

Preparation of 3"-desmethyl-5-O-mycaminosyl-6-deoxy-azithromycin using a blocked mutant of Saccharopolyspora erythraea (eryBIII/eryCIV The feeding of 6-deoxy-azithromycin agycone (Example 4) to a blocked mutant of Saccharopolyspora erythraea (eryBIII/eryCIV) produces 3"-desmethyl-5-O-mycaminosyl-6-deoxy-azithromycin. Fermentation and extraction procedures such as those described in Example 1 are easily adapted for this process.

Example 23

Preparation of 5-O-mycaminosyl-6-deoxy-N-desmethyl-azithromycin using a blocked mutant of Saccharopolyspora erythraea (eryCIV)

The feeding of 6-deoxy-N-desmethyl-azithromycin agycone (Example 4) to a blocked mutant of Saccharopolyspora erythraea (eryCIV produces 5-O-mycaminosyl-6-deoxy-N-desmethyl-azithromycin. Fermentation and extraction procedures such as those described in Example 1 are easily adapted for this process.

Example 24

Preparation of 3"-desmethyl-6-deoxy-N-desmethyl-azithromycin using a blocked mutant of Saccharopolyspora erythraea (eryBIII)

The feeding of 6-deoxy-N-desmethyl-azithromycin agycone (Example 4) to a blocked mutant of Saccharopolyspora erythraea (eryBIII) produces 3"-desmethyl-6-deoxy-N-desmethyl-azithromycin. Fermentation and extraction procedures such as those described in Example 1 are easily adapted for this process.

Example 25

Preparation of 3"-desmethyl-5O-mycaminosyl-6-deoxy-N-desmethyl-azithromycin using a blocked mutant of Saccharopolyspora erythraea (eryBIII/eryCIV)

The feeding of 6-deoxy-N-desmethyl-azithromycin agycone (Example 4) to a blocked mutant of Saccharopolyspora erythraea (eryBIII/eryCIV) produces 3"-desmethyl-5-O-mycaminosyl-6-deoxy-N-desmethyl-azithromycin. Fermentation and extraction procedures such as those described in Example 1 are easily adapted for this process.

Example 26

Generation of a blocked mutant of Saccharopolyspora crythraea (eryG)

A strain of S. erythraea is generated with a chromosomal mutation in the eryG gene following protocols established in the literature. Paulus, T. J., et al., J. Bacteriol., 172(5):2541–2546(1990). This strain is subsequently mutagenized by UV light or by chemical means using previously described methods. Hopwood, D. A., et al., Genetic Manipulations of Streptomyces A Laboratory Manual, p. 39–40 (1985). Mutagenized cells are screened on agar with a suitable indicator organism to select strains lacking antibiotic activity. Such strains are tested in agar co-synthesis experiments according to the protocol described by Spagnoli and Cappalletti (J. Antibiot., 36:365–375(1982)) to select mutants that are blocked in aglycone formation and yet are still capable of glycosylation.

Example 27

Preparation of 3-O-mycarosyl-5-O-desosaminyl-N-desmethyl-azithromycin

The feeding of azithromycin aglycone to a blocked mutant of Saccharopolyspora erythraea (eryG) produces 3-O-mycarosyl-5-O-desosaminyl-azithromycin. Fermentation and extraction procedures such as those described in Example 1 are easily adapted for this process.

What is claimed is:

1. A compound of Formula 1:

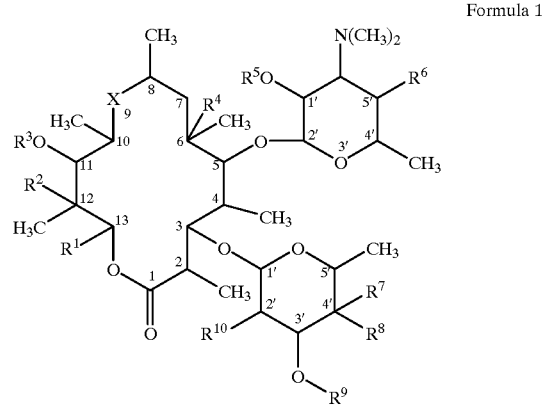

Formula 1 or a pharmaceutically acceptable salt or solvates thereof, wherein:

X is —N($R^a$)$CH_2$—, wherein the first dash of each of the foregoing X groups is attached to the C-10 carbon of the compound of Formula 1 and the last dash of each group is attached to the C-8 carbon of the compound of Formula 1, and $R^a$ is H, $C_1$–$C_{10}$ alkyl, $C_2$–$C_{10}$ alkenyl, $C_2$–$C_{10}$ alkynyl, —$(CH_2)_m(C_6$–$C_{10}$ aryl), and —$(CH_2)_m$(5–10 membered heteroaryl), wherein m is an integer ranging from 0 to 4;

$R^1$ is straight-chain or alpha-branched $C_1$–$C_8$ alkyl, alkenyl, alkynyl, alkoxyalkyl or alkylthioalkyl group any of which may be substituted by one or more hydroxyl groups; a $C_3$–$C_8$ cycloalkyl or $C_5$–$C_8$ cycloalkenyl group, either of which may be substituted by methyl or one or more hydroxyl or one or more $C_1$–$C_4$ alkyl groups or halo atoms; or a 3 to 6 membered oxygen or sulphur containing heterocyclic ring which may be saturated, or fully or partially unsaturated, and which may be substituted by one or more $C_1$–$C_4$ alkyl groups or halo atoms or a group of the formula $SR^b$, wherein $R^b$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo or a 3 to 6 membered oxygen or sulfur containing heterocyclic ring which may be saturated, or fully or partially unsaturated and which may be substituted by one or more $C_1$–$C_4$ alkyl groups or halo atoms;

or $R^1$ is phenyl which may be substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano;

or $R^1$ is of the formula

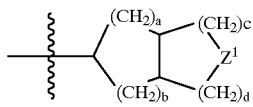

wherein $Z^1$ is O, S or —$CH_2$—, and a, b, c, and d is each independently an integer ranging from 0 to 2 and a+b+c+d#5;

$R^2$ is H or OH;

$R^3$ is H or —C(O)N$R^cR^d$, wherein each of $R^c$ and $R^d$ is independently H, $C_1$–$C_{10}$ alkyl, $C_2$–$C_{20}$ alkenyl, $C_2$–$C_{10}$ alkynyl, —$(CH_2)_m(C_6$–$C_{10}$ aryl), or —$(CH_2)_m$ (5–10 membered heteroaryl), wherein m is an integer ranging from 0 to 4, and wherein each of the foregoing $R^c$ and $R^d$ groups, except H, may be substituted by 1 to 3 Q groups; or wherein $R^c$ and $R^d$ may be taken together to form a 4–7 membered saturated ring or a 5–10 membered heteroaryl ring, wherein said saturated and heteroaryl rings may include 1 or 2 heteroatoms selected from O, S and N, in addition to the nitrogen to which $R^c$ and $R^d$ are attached, and said saturated ring may include 1 or 2 carbon-carbon double or triple bonds, and said saturated and heteroaryl rings may be substituted by 1 to 3 Q groups;

or $R^2$ and $R^3$ taken together form a carbonate ring;

$R^4$ is H, OH, O($C_1$–$C_{10}$ alkyl);

$R^5$ is H, —C(O)$R^e$, —C(O)O$R^e$, —C(O)N$R^eR^f$, or a hydroxy protecting group, and $R^e$ and $R^f$ is each independently H or $C_1$–$C_6$ alkyl;

$R^6$ is H or OH;

$R^7$ is H or OH;

$R^8$ is $C_1$–$C_{10}$ alkyl, $C_2$–$C_{20}$ alkenyl, $C_2$–$C_{10}$ alkynyl, cyano, —$CH_2S(O)_nR^g$ wherein n is an integer ranging from 0 to 2, —$CH_2OR^g$, —$CH_2N(OR^h)R^g$, —$CH_2NR^gR^i$, —$(CH_2)_m(C_6$–$C_{12}$ aryl), or —$(CH_2)_m$ (5–10 membered heteroalkyl), wherein m is an integer ranging from 0 to 4, and wherein the foregoing $R^8$ groups may be substituted by 1 to 3 Q groups;

each $R^g$ is independently H, $C_1$–$C_{10}$ alkyl, $C_2$–$C_{10}$ alkenyl, $C_2$–$C_{10}$ alkynyl, —$(CH_2)_qCR^{g(1)}R^{g(2)}(CH_2)_rNR^{g(3)}R^{g(4)}$ wherein q and r is each independently an integer ranging from 0 to 3 except q and r are not both 0, —$(CH_2)_m(C_6$–$C_{10}$ aryl), or —$(CH_2)_m$(5–10 membered heteroaryl), wherein m is an integer ranging from 0 to 4, and wherein the foregoing $R^g$ groups, except H, may be substituted by 1 to 3 Q groups;

each of $R^{g(1)}$, $R^{g(2)}$, $R^{3(3)}$ and $R^{g(4)}$ is independently selected from H, $C_1$–$C_{10}$ alkyl, —$(CH_2)_m(C_6$–$C_{10}$ aryl), or —$(CH_2)_m$(5–10 membered heteroaryl), wherein m is an integer ranging from 0 to 4, and wherein the foregoing $R^{g(1)}$, $R^{g(2)}$, $R^{g(3)}$ and $R^{g(4)}$ groups, except H, may be substituted by 1 to 3 Q groups;

or $R^{g(1)}$ and $R^{g(3)}$ are taken together to form —$(CH_2)_p$— wherein p is an integer ranging from 0 to 3 such that a 4–7 membered saturated ring is formed that may include 1 or 2 carbon-carbon double or triple bonds;

or $R^{g(3)}$ and $R^{g(4)}$ are taken together to form a 4–10 membered monocyclic or polycyclic saturated ring or a 5–10 membered heteroaryl ring, wherein said saturated and heteroaryl rings may include 1 or 2 heteroatoms selected from O, S and N, in addition to the nitrogen to which $R^{g(3)}$ and $R^{g(4)}$ are attached, said saturated ring may include 1 or 2 carbon-carbon double or triple bonds, and said saturated and heteroaryl rings may be substituted by 1 to 3 Q groups;

$R^h$ is H or $C_1$–$C_6$ alkyl;

$R^i$ is H, $C_1$–$C_{10}$ alkyl, $C_2$–$C_{10}$ alkenyl, or $C_2$–$C_{10}$ alkynyl, wherein the foregoing $R^i$ group may be substituted by 1 to 3 substituents independently selected from halo, OH, and O($C_1$–$C_6$ alkyl);

and if $R^8$ is —$CH_2NR^gR^i$, then $R^g$ and $R^i$ may be taken together to form a 4–10 membered saturated monocyclic or polycycic saturated ring or a 5–10 membered heteroaryl ring, wherein said saturated and heteroaryl rings may include 1 or 2 heteroatoms selected from O, S and N, in addition to the nitrogen to which $R^g$ and $R^i$ are attached, said saturated ring may include 1 or 2 carbon-carbon double or triple bonds, and said saturated and heteroaryl rings may be substituted by 1 to 3 Q groups;

or $R^7$ and $R^8$ are taken together to form an oxazolyl ring as shown below

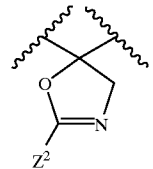

wherein $Z^2$ is —$SR^g$, —$(CH_2)_nC(O)R^g$ wherein n is 0 or 1, $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the foregoing $Z^2$ groups may be substituted by 1 to 3 Q groups;

each Q is independently selected from halo, cyano, nitro, trifluoromethyl, azido, —C(O)$Q^1$, —OC(O)$Q^1$, —C(O)O$Q^1$, —OC(O)O$Q^1$, —N$Q^2$C(O)$Q^3$, —C(O)N$Q^2Q^3$, —N$Q^2Q^3$, hydoxy, $C_1$–$C_6$ alkyl, $C_1$–$C_6$ alkoxy, —$(CH_2)_m(C_6$–$C_{10}$ aryl), and —$(CH_2)_m$(5–10 membered heteroaryl), wherein m is an integer ranging from 0 to 4, and wherein said aryl and heteroaryl substituents may be substituted by 1 or 2 subsfituents independently selected from halo, cyano, nitro, trifluoromethyl, azide, —C(O)$Q^1$, —C(O)O$Q^1$, —OC(O)O$Q^1$, —N$Q^2$C(O)$Q^3$, —C(O)N$Q^2Q^3$, —N$Q^2Q^3$, hydroxy, $C_1$–$C_6$ alkyl, and $C_1$–$C_6$ alkoxy;

each $Q^1$, $Q^2$ and $Q^3$ is independently selected from H, OH, $C_1$–$C_{10}$ alkyl, $C_1$–$C_6$ alkoxy, $C_2$–$C_{10}$ alkenyl, $C_2$–$C_{10}$ alkynyl, —$(CH_2)_m(C_6$–$C_{10}$ aryl), and —$(CH_2)_m$(5–10 membered heteroaryl), wherein m is an integer ranging from 0 to 4;

$R^9$ is H or $CH_3$; and $R^{10}$ is H or $CH_3$.

2. The compound of claim 1 with the proviso that $R^9$ is not $CH_3$ when X is —$CH_2N(R^a)$—, or —N($R^a$)CH2—, $R^6$ is H, and $R^{10}$ is $CH_3$.

3. The compound of claim 1 with the proviso that $R^9$ is not $CH_3$ when X is —C(O)—, $R^4$ is OH or $OCH_3$, $R^6$ is H, and $R^{10}$ is $CH_3$.

4. The compound of claim 1 wherein $R^a$ is H.

5. The compound of claim 1 wherein $R^1$ is ethyl, isopropyl, sec-butyl, cyclopropyl, cyclobutyl, cyclopentyl, methylthioethyl and 3-furyl.

6. The compound of claim 1 wherein $R^2$ is OH.

7. The compound of claim 1 wherein $R^3$ is H.

8. The compound of claim 1 wherein $R^4$ is H, OH or $OCH_3$.

9. The compound of claim 1 wherein $R^5$ is H or C(O)$CH_3$.

10. The compound of claim 1 wherein $R^6$ is H.
11. The compound of claim 1 wherein $R^7$ is H.
12. The compound of claim 1 wherein $R^8$ is H or OH.
13. The compound of claim 1 wherein $R^9$ is H or $CH_3$.
14. The compound of claim 1 wherein $R^{10}$ is H.
15. The compound of claim 1 wherein $R^2$ is H, $R^7$ is H, $R^8$ is OH, and $R^1$ is methyl, ethyl, isopropyl, cyclopropyl, sec-butyl, methylthioethyl, or 3-furyl.
16. The compound of claim 1 wherein $R^4$ is hydroxy, $R^5$ is H, $R^7$ is hydroxy, and $R^8$ is —$CH_2NR^gR^i$ or —$CH_2SR^g$.
17. The compound of claim 1 wherein $R^4$ is hydroxy, $R^5$ is H, $R^7$ is hydroxy, $R^8$ is —$CH_2NR^gR^i$ or —$CH_2SR^g$, and $R^i$ and $R^g$ are each selected from H, $C_1$–$C_{10}$ alkyl, $C_2$–$C_{10}$ alkenyl, and $C_2$–$C_{10}$ alkynyl, wherein the $R^i$ and $R^g$ groups, except H, may be substituted by 1 or 2 substituents independently selected from hydroxy, halo and $C_1$–$C_6$ alkoxy.
18. The compound of claim 17 wherein $R^i$ is either H or is selected from the following groups from which $R^g$ is also independently selected: methyl, ethyl, allyl, n-butyl, isobutyl, 2-methoxyethyl, cyclopentyl, cyclobutyl, 3-methoxypropyl, 3-ethoxypropyl, n-propyl, isopropyl, 2-hydroxyethyl, cyclopropyl, 2,2,2-trifluoroethyl, 2-propynyl, sec-butyl, tert-butyl, and n-hexyl. The compound of claim 1 wherein $R^4$ is hydroxy, $R^5$ is H, $R^7$ is hydroxy, $R^8$ is —$CH_2NHR^g$, and $R^9$ is —$(CH_2)_m(C_6$–$C_{10}$ aryl) wherein m is an integer ranging from 0 to 4.
19. The compound of claim 18 wherein $R^g$ is phenyl or benzyl.
20. The compound of claim 1 wherein $R^4$ is hydroxy, $R^5$ is H, $R^7$ is hydroxy, $R^8$ is —$CH_2SR^g$, and $R^g$ is selected from $C_1$–$C_{10}$ alkyl, $C_2$–$C_{10}$ alkenyl, and $C_2$–$C_{10}$ alkynyl, wherein said $R^g$ groups may be substituted by 1 or 2 substituents independently selected from hydroxy, halo and $C_1$–$C_6$ alkoxy.
21. The compound of claim 20 wherein $R^g$ is methyl, ethyl or 2-hydroxyethyl.
22. The compound of claim 1 wherein $R^4$ is hydroxy, $R^5$ is H, $R^7$ is hydroxy, and $R^8$ is —$(CH_2)_m$(5–10 membered aryl) wherein m is an integer ranging from 0 to 4.
23. The compound of claim 22 wherein $R^8$ is phenyl.
24. The compound of claim 1 wherein $R^8$ is of the formula:

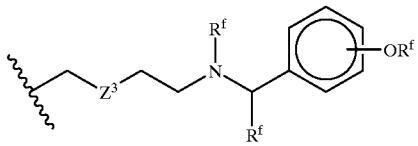

wherein $Z^3$ is O, S, or —$N(R^i)$—, and wherein the —$OR^h$ group may be attached at any available carbon on the phenyl group.

25. A pharmaceutical composition comprising a therapeutically effective amount of a compound of claim 1, 2, 3, or 4 and a pharmaceutically acceptable carrier.

26. A method of treating, mitigating or preventing bacterial or protozoal infections in mammals, fish or birds which comprises the administration of a therapeutically effective amount of a compound of claim 1, 2, 3, or 4.

27. A method of treating, mitigating or preventing cancer in mammals, fish or birds which comprises the administration of a therapeutically effective amount of a compound of claim 1, 2, 3, or 4.

28. A method of preparing an azalide compound having at least one sugar comprising contacting an azalide aglycone compound with a biological culture under conditions suitable for the formation of an azalide having at least one sugar, and isolating from the biological culture an azalide having at least one sugar.

29. The method of claim 28 further comprising selecting the biological culture to be a biological culture of *Streptomyces antibioticus* ATCC 202189, *Saccharopolyspora erythraea* ATCC 202199, or a blocked mutant of a *Saccharopolyspora erythraea* strain comprising at least one eryCIV or eryBIII mutation, or a mixture of at least one eryCIV and at least one eryBIII mutation.

30. The method of claim 29 wherein X is —$CH_2N(R^a)$— or —$N(R^a)CH_2$—.

31. The method of claim 29 further comprising selecting the biological culture to be a biological culture of *Streptomyces antibioticus* ATCC 202189, *Saccharopolyspora erythraea* ATCC 202199, or a blocked mutant of a *Saccharopolyspora erythraea* strain comprising at least one eryCIV or eryBIII mutation, or a mixture of at least one eryCIV and at least one eryBIII mutation.

32. The method of claim 29 further comprising preparing the compound of Formula 3 from a compound of Formula 4:

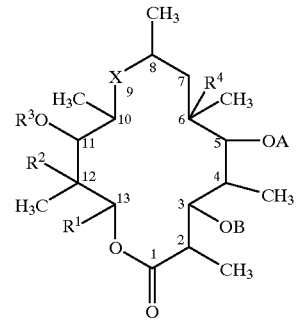

Formula 4 wherein X, $R^1$, $R^2$, $R^3$, and $R^4$ are defined above; A is of the formula:

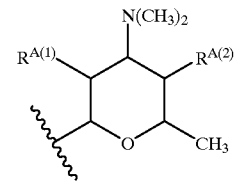

wherein each of $R^{A(1)}$ and $R^{A(1)}$ is independently H, OH, $C_1$–$C_6$ alkyl, aldehyde, ketone, ester, carboxylic acid, carbamate, or derivatives thereof; and B is a sugar.

33. The method of claim 31 wherein B is a sugar of the formula:

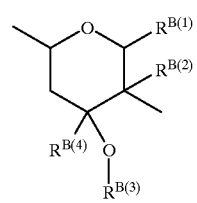

wherein each of $R^{B(1)}$ and $R^{B(2)}$ is independently H, OH, $C_1$–$C_6$ alkyl, aldehyde, ketone, ester, carboxylic acid, amine, or derivatives thereof, and each of $R^{B(3)}$ and $R^{B(4)}$ is independently H or $CH_3$.

* * * * *